(12) United States Patent
Aarts et al.

(10) Patent No.: US 10,596,103 B2
(45) Date of Patent: Mar. 24, 2020

(54) DRUG DELIVERY SYSTEM FOR DELIVERY OF ANTI-VIRALS

(71) Applicants: Merck Sharp & Dohme B.V., Haarlem (NL); Dennis Aarts, Etten-Leur (NL); Wouter de Graaff, Sprang-Capelle (NL); Johannes Antonius Hendrikus van Laarhoven, Vught (NL)

(72) Inventors: Dennis Aarts, Etten-Leur (NL); Wouter de Graaff, Sprang-Capelle (NL); Johannes Antonius Hendrikus van Laarhoven, Vught (NL)

(73) Assignee: Merek Sharp & Dohme B.V., Haarlem (NL)

( * ) Notice: Subject to any disclaimer, the term of this patent is extended or adjusted under 35 U.S.C. 154(b) by 168 days.

(21) Appl. No.: 15/036,839

(22) PCT Filed: Dec. 8, 2014

(86) PCT No.: PCT/EP2014/076821
§ 371 (c)(1),
(2) Date: May 16, 2016

(87) PCT Pub. No.: WO2015/086489
PCT Pub. Date: Jun. 18, 2015

(65) Prior Publication Data
US 2016/0296467 A1   Oct. 13, 2016

Related U.S. Application Data

(60) Provisional application No. 61/914,438, filed on Dec. 11, 2013.

(30) Foreign Application Priority Data

Dec. 11, 2013   (EP) .................................. 13196739.0

(51) Int. Cl.
| | | |
|---|---|---|
| A61K 9/00 | (2006.01) | |
| A61K 47/32 | (2006.01) | |
| A61K 31/5025 | (2006.01) | |
| A61K 31/506 | (2006.01) | |
| A61K 45/06 | (2006.01) | |
| A61K 31/57 | (2006.01) | |
| A61K 31/567 | (2006.01) | |

(52) U.S. Cl.
CPC .......... *A61K 9/0036* (2013.01); *A61K 31/506* (2013.01); *A61K 31/5025* (2013.01); *A61K 31/567* (2013.01); *A61K 31/57* (2013.01); *A61K 45/06* (2013.01); *A61K 47/32* (2013.01)

(58) Field of Classification Search
None
See application file for complete search history.

(56) References Cited

U.S. PATENT DOCUMENTS

| | | |
|---|---|---|
| 3,545,439 A | 12/1970 | Duncan et al. |
| 3,854,480 A | 12/1974 | Zaffaroni et al. |
| 3,995,633 A | 12/1976 | Gougeon et al. |
| 3,995,634 A | 12/1976 | Drobish et al. |
| 4,237,885 A | 12/1980 | Wong et al. |
| 4,292,965 A | 10/1981 | Nash et al. |
| 4,596,576 A | 6/1986 | de Nijs |
| 4,629,449 A | 12/1986 | Wong |
| 4,666,702 A | 5/1987 | Junginger |
| 5,840,771 A | 11/1998 | Oldham et al. |
| 5,851,547 A | 12/1998 | Fujioka et al. |
| 5,972,372 A | 10/1999 | Saleh et al. |
| 5,989,581 A | 11/1999 | Groenewegen |
| 6,544,546 B1 | 4/2003 | Groenewegen |
| 6,579,533 B1 | 6/2003 | Tormala et al. |
| 6,590,081 B1 | 7/2003 | Ihang |
| 6,831,073 B1 | 12/2004 | Lanquetin et al. |
| 6,906,049 B1 | 6/2005 | Paris et al. |
| 7,749,987 B2 | 7/2010 | Paris et al. |
| 2003/0059456 A1 | 3/2003 | Malcolm et al. |
| 2004/0062804 A1 | 4/2004 | Lee et al. |
| 2006/0252835 A1 | 11/2006 | Broquaire et al. |
| 2006/0280771 A1 | 12/2006 | Groenewegn et al. |
| 2007/0197478 A1* | 8/2007 | Jones ................... C07D 213/75 514/81 |
| 2008/0242650 A1 | 10/2008 | Thomas |

(Continued)

FOREIGN PATENT DOCUMENTS

| | | |
|---|---|---|
| EP | 0050867 B1 | 1/1988 |
| EP | 0279982 A1 | 8/1988 |
| EP | 0303306 B1 | 3/1993 |

(Continued)

OTHER PUBLICATIONS

Kaur, M, Delivery of Entry Inhibitors Using Intravaginal Rings for Previnting the Sexual Transmission of HIV, The University of Utah Graduate School, 2009, p. 1-84, 00.

Davies, G. C. et al, Ovarian Activity and Bleeding Patterns During Extended Continuous Use of a Combined Contraceptive Vaginal Ring, Contraception, 1992, p. 269-278, vol. 46.

Davies, G. C. et al, The Effects of a Combined Contraceptive Vaginal Ring Releasing Ethinyloestradiol and 3-Ketodesogestrel on Vaginal Flora, Contraception, 1992, p. 511-518, vol. 45.

Di Fabio, S. et al, Inhibition of vaginal transmission of HIV-1 in hu-SCID mice by the non-nucleoside reverse transcriptase inhibitor TMC120 in a gel formulation, AIDS, 2003, p. 1597-1604, vol. 17.

Keskar, V. et al, Cervical cancer treatment with a locally insertable controlled release delivery system, Journal of Controlled Release, 2006, p. 280-288, vol. 115.

(Continued)

*Primary Examiner* — Nicole P Babson
(74) *Attorney, Agent, or Firm* — Janet E. Fair; Catherine D. Fitch

(57) ABSTRACT

Described herein is a vaginal ring drug delivery system comprising (i) a core comprising a first thermoplastic polymer and a first therapeutic agent, wherein the first therapeutic agent is dissolved in the first thermoplastic polymer, and (ii) a skin surrounding the core comprising a second thermoplastic polymer and a second therapeutic agent, wherein the second therapeutic agent is in solid form.

7 Claims, 18 Drawing Sheets

(56) References Cited

U.S. PATENT DOCUMENTS

2011/0305662 A1* 12/2011 Verdin .................. A61K 31/15 424/85.2

FOREIGN PATENT DOCUMENTS

| EP | 0876815 B1 | | 1/2002 |
|---|---|---|---|
| WO | WO1989009066 A1 | | 10/1989 |
| WO | WO1997002015 A1 | | 1/1997 |
| WO | WO1999030976 A1 | | 6/1999 |
| WO | WO2003017971 A1 | | 3/2003 |
| WO | WO 2004/103336 | * | 12/2004 |
| WO | WO2004103336 A2 | | 12/2004 |
| WO | WO2005004837 A1 | | 1/2005 |
| WO | WO2005089723 A1 | | 9/2005 |
| WO | WO2007001888 A2 | | 1/2007 |
| WO | WO2008100876 A1 | | 8/2008 |
| WO | WO2009035562 A2 | | 3/2009 |
| WO | WO2012080195 A2 | | 6/2012 |
| WO | WO2013120888 A2 | | 8/2013 |
| WO | WO2015086491 A1 | | 6/2015 |

OTHER PUBLICATIONS

Kim. H. et al, Application of Binary Polymer System in Drug Release Rate Modulation. 2. Influence of Formulation Variables and Hydrodynamic Conditions on Release Kinetics, Journal of Pharmaceutical Sciences, 1997, p. 323-328, vol. 86, No. 3.

Kubba, A. et al., Contraception, The Lancet, 2000, p. 1913-1919, vol. 356.

Ladipo, O. et al, Contraceptive implants, Current Opinion in Obstetrics and Gynecology, 1994, p. 564-569, vol. 6.

Madan, R. P. et al, Prioritizing prevention of HIV and sexually transmitted infections: first-generation vaginal microbicides, Curr Opin Infect Dis, 2006, p. 49-54, vol. 19.

Malcolm, K. et al., In vitro release of nonoxynol-9 from silicone matrix intravaginal rings, Journal of Controlled Release, 2003, p. 355-364, vol. 91.

Malcolm, R. K., et al., Vaginal rings for delivery of HIV Microbicides, International Journal of Women's Health, 2012, p. 595-605, 4.

Niascimento, M. D. L. P. et al, Nomegestrol acetate contraceptive implant use by women with sickle cell disease, Clin Pharmacol Ther, 1998, p. 433-438, vol. 64.

Skoler-Karpoff, S. et al, Efficacy of Carraguard for prevention of HIV infection in women in South Africa: a randomised, double-blind, placebo-controlled trial, The Lancet, 2008, p. 1977-1987, vol. 372.

Van Damme, L. et al, Lack of Effectiveness of Cellulose Sulfate Gel for the Prevention of Vaginal HIV Transmission, The New England Journal of Medicine, 2008, p. 463-472, vol. 359.

Van Laarhoven, J.A.H. et al, Effect of supersaturation and crystallization phenomena on the release properties of a controlled release device based on EVA copolymer, Journal of Controlled Release, 2002, p. 309-317, vol. 82.

Van Laarhoven, J.A.H., et al., In vitro release properties of etonogestrel and ethinyl estradiol from a contraceptive vaginal ring, International Journal of Pharmaceutics, 2002, p. 163-173, vol. 232.

Woolfson, A.D. et al, Design of a silicone reservoir intravaginal ring for the delivery of oxybutynin, Journal of Controlled Release, 2003, p. 465-476, vol. 91.

Woolfson, A.D. et al., Design of an intravaginal ring for the controlled delivery of 17B-estradiol as its 3-acetate ester, Journal of Controlled Release, 1999, p. 319-328, vol. 61.

Zaneveld, L. J. D. et al., Use of mandelic acid condensation polymer (SAMMA), a new antimicrobial contraceptive agent, for vaginal prophylaxis, Fertility and Sterility, 2002, p. 1107-1115, vol. 78, No. 5.

* cited by examiner

DRUG DELIVERY SYSTEM FOR DELIVERY OF ANTI-VIRALS

CROSS-REFERENCE TO RELATED APPLICATIONS

This application is a U.S. National Phase application under 35 U.S.C. § 371 of PCT Application No. PCT/EP2014/076821, filed Dec. 08, 2014, which published as WO 2015/086489 Al on Jun. 18, 2015, and claims priority under 35 U.S.C. § 365(b) from United States provisional patent application No. 61/914438, filed Dec. 11, 2013 and European provisional patent application No. 13196739.0, filed Dec. 11, 2013.

FIELD OF THE INVENTION

The present invention relates to the field of prevention of the transmission of HIV and for preventing AIDS. More particularly, the present invention relates to a vaginal ring, for the simultaneous release of two or more therapeutic agents designed to prevent HIV in a substantially constant ratio over a prolonged period of time.

BACKGROUND

The lack of proper medicaments to prevent and/or stop the spread of HIV among sexual partners has been well documented. See J. Cohen, Science, (Oct. 15, 2004) 306; J. Turpin, Expert. Opin. Investig. Drugs, (August 2002) 11(8), 1077-1097; R. Trager, Science, (Jan. 3, 2003), 299. Infection with HIV leads to Acquired Immunodeficiency Syndrome ("AIDS") or AIDS Related Complex ("ARC") in over 90% of untreated infected individuals within a ten-year period. As the HIV epidemic continues to threaten millions of people worldwide, new strategies to prevent the spread of the virus are desperately needed. In the absence of an effective preventative vaccine, alternative methods of preventing HIV infection are currently being explored.

HIV typically establishes an infection by first attaching to CD4 receptors on white blood cells and then grabbing a second receptor known as CC Chemokine Receptor 5 ("CCR5"), which normally responds to immune chemicals called chemokines. Epidemiological and viral transmission studies have shown that viruses using the CCR5 receptor are often associated with transmission of HIV infection between individuals. Therefore blocking these viruses by prophylactic treatment with a specific CCR5 inhibitor should prove an effective way to prevent HIV transmission in a susceptible population. For example, M. Lederman et al, Science (Oct. 15, 2004) 306, 485-487 describe a study of the ability of N.sup.alpha.-(n-nonanoyl)-des-Ser.sup.1-[L-thioproline-.sup.2, L-.alpha.-cyclohexyl-glycine.sup.3] RANTES ("PSC-RANTES") to prevent acquisition of SHIV infection at a mucosal skin. Q. Hu et al, J. Exp. Med. (Apr. 19, 2004) 199(8), 1065-1075 describe the blockade of the effect of both CCR5 and CXCR4 to prevent infection.

However, successful prevention of HIV infection may be best achieved with using a combination of anti-virals which each prevent infection through a different mechanism. Thus combining a CCR5 inhibitor with antiviral compounds which act as inhibitors of HIV replication can be effective methods of preventing HIV infections. Such inhibitors of HIV replication include reverse transcriptase inhibitors such as azidothymidine (AZT) and efavirenz and protease inhibitors such as indinavir and nelfinavir. Integrase has also shown to play a role in viral replication. The inhibition of integrase in vitro and of HIV replication in cells is a direct result of inhibiting the strand transfer reaction catalyzed by the recombinant integrase in vitro in HIV infected cells.

One solution to the need to administer CCR5 receptor antagonists in combination with an inhibitor of HIV integrase or other inhibitors of HIV replication in an intravaginal ring (IVR). However, simultaneous drug release of two or more therapeutic agents from an IVR is challenging because two or more drugs have to be released from one device and multiple sets of pre-defined drug release criteria must be fulfilled in order for the system to be effective. Several different IVR designs have attempted to provide specific controlled release solutions, mostly for contraceptives, but few have been successful.

Most, if not all of the current IVRs, including those described in the following patents and applications: U.S. Pat. Nos. 3,995,633; 3,995,634; 4,237,885; European patent publication 0,050,867; U.S. Pat. Nos. 4,292,965; 4,596,576; PCT publication WO 97/02015; European Patent 876 815; PCT publication WO2009/036999 and PCT publication WO2004/103336, suffer from at least one of the following drawbacks: lack of stability upon storage and transport, inability to independently adjust the release rate of multiple therapeutic components, difficulty or expense in manufacturing, inability to meet necessary release criteria to achieve the desired therapeutic effect and complexity of design.

Examples of known IVRs are described in scientific literature, e.g. Malcolm et al, Vaginal rings for delivery of HIV microbicides, International Journal of Women's Health, 2012:4 595-605, gives an overview of the current state-of-the-art in microbicide delivery via IVRs. Several complex solutions for releasing multiple compounds are described such as the "pod-ring" and the multi segmented polyurethane ring. In addition, reference is made to the disadvantages of the so-called reservoir rings compared to matrix type rings. Most notably their complex manufacture and low release rates.

The systems disclosed in EP 876 815 and the PCT publications WO2009/036999 and WO2004/103336 set the standard when manufacturability of IVRs suitable for simultaneous drug release at large-scale is concerned. Specifically, WO2004/103336 discloses a reservoir type drug delivery system comprising at least one compartment consisting of (i) a drug-loaded thermoplastic polymer core, (ii) a drug-loaded thermoplastic polymer intermediate layer and (iii) a non-medicated thermoplastic polymer skin covering the intermediate layer, wherein said intermediate layer is loaded with (a) crystals of a first pharmaceutically active compound and with (b) a second pharmaceutically active compound in dissolved form and wherein said core is loaded with said second compound in dissolved form.

Although the system disclosed in WO2004/103336 is suitable for the independent release of many drug combinations, the latter can still be improved upon particularly with regard to the capacity of releasing a wide range of drugs, including anti-virals, at sufficiently high rates to achieve the desired therapeutic effect.

Drug release from the WO2004/103336 system in certain cases is too much restrained by the low drug permeability of the rate limiting skin surrounding the reservoir. Additionally, examples exemplified in WO2004/103336 include a diffusion path through the membrane which is identical for all drugs loaded in the reservoir. As a consequence varying membrane properties will affect all drugs essentially equally and hence the release is tuned in the same direction—all up or all down—and the ratio in which the dissolved and crystalline drug are released remains essentially unaffected.

Additionally, the IVRs exemplified in WO2004/103336 suffer from the further limitation that the release of the dissolved drug is tuned to its desired rate by dissolving the right amount in the reservoir. It appears that this specific amount, resulting in the exact right concentration needed to obtain the desired release, is directly proportional with the saturation solubility ($C_{A,s}$) and inversely proportional with the release rate of the crystalline drug (dMa/dt). Low saturation solubility means a small driving force for diffusion and hence higher release rates for the crystalline drug can only be achieved if thin skins are applied. The release of drug depends on the amount dissolved and on the thickness of the skin. If the same target release rate for drug is to be matched with a thinner skin, less of drug should be dissolved in the core. So, the flipside of applying too thin skins is that the amount of dissolved drug becomes too small resulting in early depletion and steeply declining release profiles hampering broad application of the concept disclosed in WO200/103336.

This phenomenon can also be explained mathematically. The steady state drug release rate for cylindrical reservoir systems can be described mathematically by the following equation:

$$\frac{dM}{dt} = \frac{2\pi L D \Delta C}{\ln\left(\frac{r_0}{r_i}\right)} \quad (1)$$

in which:
dM/dt is the release rate [kg/s]
L is the length of the cylinder [m]
r0 is outer radius of the skin [m]
ri is the inner radius of the skin [m]
D is the drug in polymer diffusion coefficient m2/s
ΔC is the concentration gradient over the skin [kg/m3]
DΔC Is drug permeability kg/m·s For thin layers equation (1) can be approximated by:

$$\frac{dM}{dt} = \frac{2\pi L D \Delta C}{d} \quad (2)$$

in which d is the skin thickness [m]
From equation (2) it follows that the skin thickness is proportional with the drug permeability (DΔC) and inversely proportional with drug release (dM/dt) rate:

$$d \propto \frac{D \Delta C}{\frac{dM}{dt}} \quad (3)$$

Under sink conditions the concentration at the skin surface (r=r₀) is zero and equation (3) reduces to:

$$d \propto \frac{D \cdot C}{\frac{dM}{dt}}, \quad (4)$$

where C is the concentration in the skin at the interface (r=$r_i$)

In WO2004/103336 the crystalline drug in the intermediate layer and the dissolved drug loaded in core and intermediate layer pass through the same skin, hence the following condition (5) holds:

$$d \propto \frac{D_B \cdot C_B}{\frac{dM_B}{dt}} = \frac{D_A \cdot C_{A,s}}{\frac{dM_A}{dt}} \quad (5)$$

in which;
dMA/dt The release rate of the crystalline drug (A) [kg/s]
dMB/dt The release rate of the dissolved drug (B) [kg/s]
d Skin thickness [m]
DA Diffusion coefficient of the crystalline drug (A)
DB Diffusion coefficient of the dissolved drug (B)
CB The concentration of the completely dissolved drug
CA,s Saturation concentration of the crystalline drug From equation (5) follows the required concentration of the dissolved drug (B):

$$C_B = \frac{\frac{dM_B}{dt}}{\frac{dM_A}{dt}} x \frac{D_A}{D_B} x C_{A,s} \quad (6)$$

Based on mechanistic considerations it can be concluded that the concentration of the dissolved drug ($C_B$) needed to obtain the right release for drug B, may become critically low when the saturation solubility is relatively low and the target release rate relatively high. Equation (6) indicates that concentration of dissolved drug ($C_B$) in the reservoir proportionally depends on the saturation solubility and inversely on the release rate of the crystalline drug ($dM_A$/dt). Hence $C_B$ decreases with decreasing saturation solubility $C_{A,s}$ and increasing release rate $dM_A$/dt of the crystalline drug A. The drug-in-polymer diffusion coefficients in equation 6 are an intrinsic property of the polymer-drug pairs and hence these parameters may only coincidentally help to move $C_B$ in a higher direction. It can be concluded that $C_B$ and hence the amount of dissolved drug B in the delivery system, is tied by the solubility and release rate of drug A. If the amount of drug B dissolved in the reservoir is below a certain level, the release cannot be sustained over the intended duration of use. Certain embodiments of the IVRs described below are designed to overcome this and the other above limitations.

SUMMARY

The key difference between the present invention and previously exemplified drug delivery systems, in particularly WO2004/103336, is that the vaginal ring drug delivery systems described herein include a therapeutic agent in the skin, thus the average diffusion distance of the second therapeutic agent through the skin is less than the average diffusion distance of the therapeutic agent loaded in the core. In other words, the two therapeutic agents in WO2004/103336 are both required to pass completely through a rate limiting skin which is not the case of the vaginal ring drug delivery systems described herein. The advantage of the present system is twofold; as a result of the reduced diffusion length higher release rates can be achieved for the drug loaded in the skin. Furthermore the differentiated diffusion length of the drugs loaded in the core and skin augment the possibility to affect the release of these drugs independently and to adjust the release the drugs to their respective optimal levels.

Described herein are vaginal ring drug delivery systems comprising (i) a core comprising a first thermoplastic polymer and a first therapeutic agent, wherein the first therapeutic agent is dissolved in the first thermoplastic polymer, and (ii) a skin surrounding the core comprising a second thermoplastic polymer and a second therapeutic agent, wherein the second therapeutic agent is in solid form.

DETAILED DESCRIPTION

Figure 1:
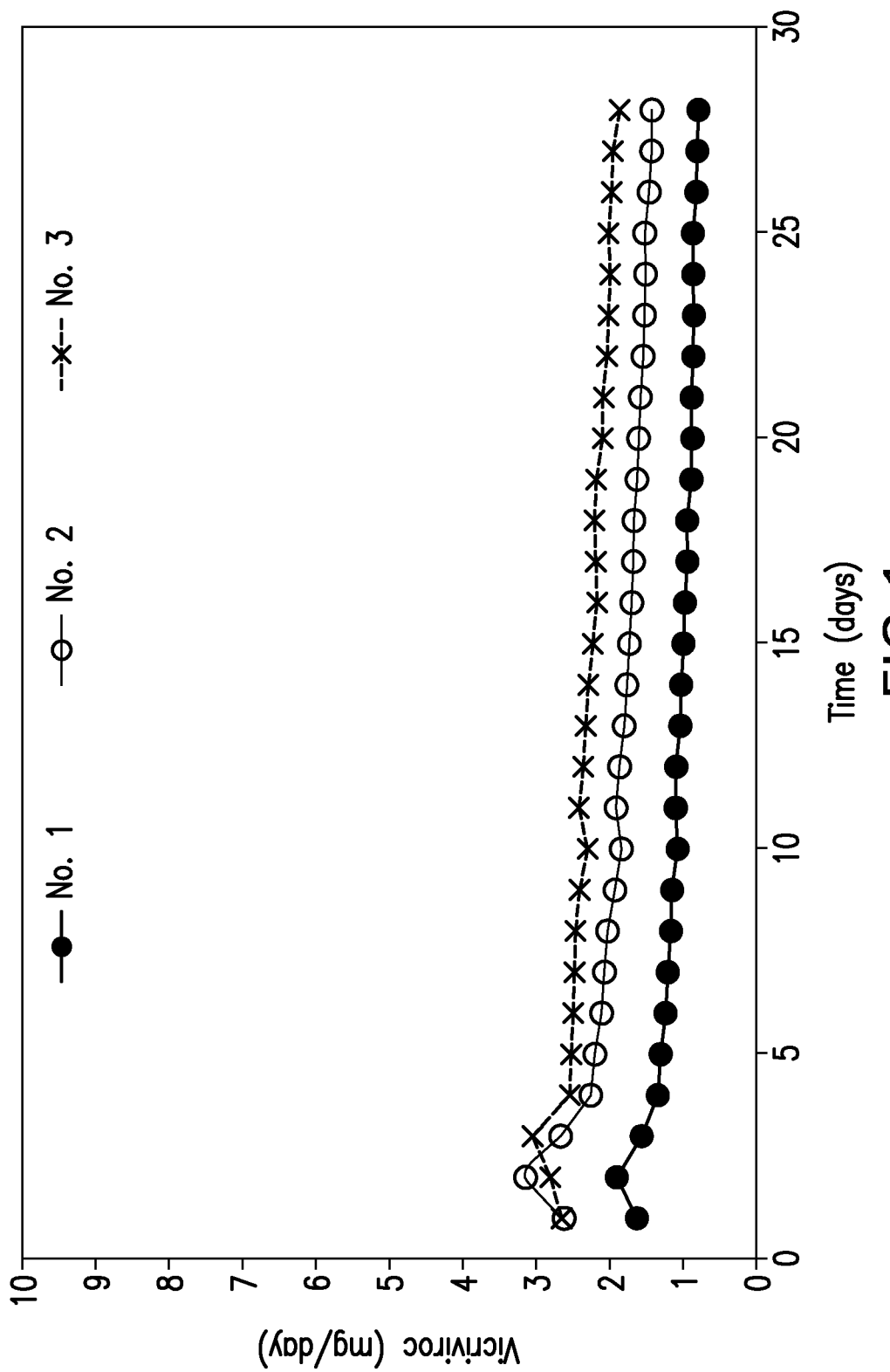
FIG. 1 show the in vitro release of vicriviroc from vaginal ring drug delivery systems exemplified herein.

The following definitions are used in the subsequent further description of the invention:

"Drug", "medicament" and "therapeutic agent" are used herein interchangeably.

"Ethylene-vinylacetate" and "EVA" are used herein interchangeably.

"Loaded" means the placement of the therapeutic upon manufacture.

"Matrix system" is defined as a system wherein a therapeutic agent is uniformly distributed in the matrix material and has no other release barrier than diffusion out of the matrix material.

"Permeability" means the measurement of a therapeutic agent's ability to pass through a thermoplastic polymer.

"Reservoir system" means a drug delivery system which includes a drug-loaded reservoir surrounded by a skin and the diffusion of the drug through the skin is rate limiting. As a result of the rate limiting properties of the skin, an almost spatially uniform concentration of dissolved drug will be maintained in the core during release, whereas a concentration gradient will develop primarily in the skin.

"Reservoir" is the interior part of the drug delivery system comprising of polymer(s) with relatively high permeability for the therapeutic agents.

"Rate limiting skin" is the part of the system which comprises of polymer(s) with relatively low permeability for the therapeutic agents. "Skin" means the outer portion of the drug delivery system that contacts the external environment. The skin can be a rate limiting depending of the composition of the skin.

"Vinylacetate" and "VA" are used herein interchangeably.

Described herein are vaginal ring drug delivery systems comprising (i) a core comprising a first thermoplastic polymer and a first therapeutic agent, wherein the first therapeutic agent is dissolved in the first thermoplastic polymer, and (ii) a skin surrounding the core comprising a second thermoplastic polymer and a second therapeutic agent, wherein the second therapeutic agent is in solid form.

Also, described herein are vaginal ring drug delivery systems comprising (i) a core comprising a first thermoplastic polymer and a first therapeutic agent, wherein the first therapeutic agent is dissolved in the first thermoplastic polymer, and (ii) a skin surrounding the core comprising a second thermoplastic polymer and a second therapeutic agent, wherein the second therapeutic agent is in solid form, wherein the first and second therapeutic agents are anti-viral agents.

In certain embodiments, the vaginal ring drug delivery systems described herein comprising the first therapeutic agent in the core and the second therapeutic agent in a skin surrounding the core, can be described as a matrix type system wherein the first thermoplastic polymer of the core and the second thermoplastic polymer of the skin are the same polymer.

In other embodiments, the vaginal ring drug delivery systems described herein comprising the first therapeutic agent in the core and the second therapeutic agent in the skin surrounding the core, can be described as a hybrid between a reservoir type system and a matrix system or alternatively an enhanced matrix-type system, wherein the first thermoplastic polymer of the core and the second thermoplastic polymer of the skin are different polymers. The therapeutic agent loaded in the core will behave like a reservoir type system and will be released in a near zero order fashion typical for reservoir systems, while the therapeutic agent loaded in the skin will exhibit a release profile more akin to a matrix-type system. It is this hybrid configuration that allows certain embodiments of the described vaginal ring drug delivery systems to meet the necessary release criteria needed to achieve the desired therapeutic effect.

In certain embodiments, of the vaginal ring drug delivery systems described herein the second therapeutic agent is loaded into the skin such that the second therapeutic agent is dispersed uniformly though out the skin.

In other embodiments, the therapeutic agent in the skin is loaded in such a way that a depletion layer, or a portion of the skin that does not comprise the second therapeutic agent, is pre-formed or built-in, and the drug loaded in the skin displays a near zero order release profile while obtaining higher release rates compared to a reservoir-type system. The depletion layer of the vaginal ring drug delivery system described herein allows the second therapeutic agent in the skin to exhibit a near zero-order release profile while allowing the second therapeutic agent in the skin to meet the necessary release criteria needed to achieve a desired therapeutic effect. Specifically, the second therapeutic agent in the skin will be released at a higher dose as compared to a drug release system wherein that same therapeutic agent had to pass through a drug-free rate limiting skin. The reason for this may be attributed to the fact that the drug incorporated in the skin only passes through the depletion layer instead of through the entire skin. Hence, the diffusion length is largely reduced but not entirely absent.

In certain embodiments, the skin comprises one layer. In other embodiments the skin comprises two layers. In still other embodiments, the skin comprises two or more layers, wherein, upon manufacture, the second therapeutic agent is loaded in a layer of the skin, creating a built-in depletion layer, and the second therapeutic agent is not completely dispersed throughout the entire skin.

For example in certain embodiments of the vaginal ring drug delivery system described herein, the skin comprises a first layer and a second layer, wherein the first layer is adjacent to the core and the second layer is adjacent to the first layer. In certain embodiments, the first layer is loaded with the second therapeutic agent and the second layer contains no therapeutic agent and acts as the depletion layer.

The thickness of the skin is determined by the concentration of the second therapeutic agent and the desired release rate of the second therapeutic agent. Suitable thicknesses of the skin can range from 5-700 μm, from 10-500 μm, from 15-450 μm, from 20-450 μm, from 30-400 μm, from 35-350 μm and from 40-300 μm. In certain embodiments the thickness of the skin is 10 μm, 20 μm, 30 μm, 40 μm, 50 μm, 60 μm, 70 μm, 80 μm, 90 μm, 100 μm, 125 μm, 150 μm, 175 μm, 200 μm, 225 μm, 250 μm and 300 μm. In some embodiments, the thickness of the skin is 30 μm, 50 μm or 80 μm.

In certain embodiments, the first layer and second layer of the skin are made from the same polymer. However, it can be envisioned that different polymers can be used for the first layer and second layer of the skin so long as the second therapeutic agent in the skin the necessary release criteria needed to achieve a desired therapeutic effect.

In other embodiments, the skin comprises three layers, a first layer adjacent to the core, a second layer adjacent to the first layer and a third layer adjacent to the second layer wherein, the second layer is loaded with the second therapeutic agent and the third layer acts as the depletion layer.

In certain embodiments, the first, second and third layers of the skin are made from the same polymer. However, it can be envisioned that different polymers can be used for the first, second and third layers of the skin so long as the second therapeutic agent in the skin meets the necessary release criteria needed to achieve a desired therapeutic effect.

In certain embodiments described herein, the core can be a single compartment, meaning the core has no layers. In other embodiments, the core of the drug delivery systems described herein comprises two layers. In other embodiments, the core of the drug delivery systems described herein comprises two layers or more. For example in certain embodiments of the vaginal ring drug delivery systems described herein, the core comprises a first layer and a second layer, wherein the second layer is adjacent to the skin and the first layer is adjacent to the second layer.

In certain embodiments, the first layer and second layer of the core are made from the same polymer. However, it can be envisioned that different polymers can be used for the first layer and second layer of the core so long as the permeability of the polymers used for the core are relatively low compared to the permeability of the polymers used for the skin.

In certain embodiments of the vaginal ring drug delivery devices described herein, a vaginal ring drug delivery device comprises (i) a core comprising a first therapeutic agent; a first thermoplastic polymer; a first core layer and a second core layer; and (ii) a skin surrounding the core comprising a second therapeutic agent; a second thermoplastic polymer; a first skin layer and a second skin layer wherein the first skin layer is between the second skin layer and the second core layer.

In other embodiments, the core comprises three layers, a third layer adjacent to the skin, a second layer adjacent to the third layer and a first layer adjacent to the second layer.

In certain embodiments, the first, second and third layers of the core are made from the same polymer. However, it can be envisioned that different polymers can be used for the first, second and third layers of the core so long as the first therapeutic agent in the core experiences a reduced permeation resistance as it is being released through the skin and meets the necessary release criteria needed to achieve a desired therapeutic effect.

In certain embodiments, the first therapeutic agent is in dissolved form in the core and the second therapeutic agent is in solid form in the skin. As used herein, solid can include crystalline or amorphous forms. In certain embodiments, the first therapeutic agent is in dissolved form in the core and the second therapeutic agent is in crystalline form in the skin. In certain embodiments, the first therapeutic agent is in dissolved form in the core and the second therapeutic agent is in amorphous form in the skin.

Suitable thermoplastic polymers that can be used in the vaginal ring drug delivery systems described herein, may, in principle, be any thermoplastic polymer or elastomer material suitable for pharmaceutical use, such as low density polyethylene, ethylene-vinylacetate copolymers, polyurethanes and styrene-butadiene-styrene copolymers. In certain embodiments, ethylene-vinylacetate copolymer (poly-EVA) is used in the core and the skin due to its excellent mechanical and physical properties. The poly-EVA material may be used for the core, as well as the skin and can be any commercially available ethylene-vinylacetate copolymer, such as the products available under the trade names: ELVAX, EVATANE, LUPOLEN, MOVRITON, ULTRATHENE, ATEVA and VESTYPAR.

In certain embodiments, the core comprises a first thermoplastic polymer and the skin comprises a second thermoplastic polymer, wherein the first and second thermoplastic polymers are made out of the same polymer. In other embodiments, the core comprises a first thermoplastic polymer and the skin comprises a second thermoplastic polymer, wherein the first and second thermoplastic polymers are made out of a different polymer grade. By electing different polymer grades for the first and second polymer the rate of release of the first therapeutic agent in the core can be adjusted.

In certain embodiments, the first thermoplastic polymer is ethylene-vinylacetate copolymer. In other embodiments, the second thermoplastic polymer is ethylene-vinylacetate copolymer. In some embodiments the core comprises a first thermoplastic polymer and the skin comprises a second thermoplastic polymer, wherein the first and second thermoplastic polymers are made out of the same ethylene-vinylacetate.

In still other embodiments, the first thermoplastic polymer and the second thermoplastic polymer each comprise an ethylene-vinylacetate copolymer, wherein the first thermoplastic polymer has a higher vinylacetate content than the second thermoplastic polymer. In general, solubility of therapeutic agents increases with increasing vinylacetate content. Thus, having a skin of ethylene-vinylacetate copolymer with a lower vinylacetate content than the vinylacetate of the core would enable the rate limiting properties of the skin.

The permeability of EVA copolymers for small to medium sized drug molecules ($M_a \leq 600$ g/mol) is primarily determined by the vinylacetate (VA) to ethylene ratio. Low-VA content EVA copolymers are substantially less permeable than high VA-content skins and hence display rate limiting properties if used as skin. EVA copolymers with VA-content of 19% m/m or less (≤19% m/m) are substantially less permeable than polymer having VA-content above and including 25% m/m (≥25% m/m).

In some embodiments, the first thermoplastic polymer is an ethylene-vinylacetate copolymer and has a vinylacetate content of 28% or greater. In other embodiments, the first thermoplastic polymer has a vinylacetate content of greater than 28%. In still other embodiments, the first thermoplastic polymer has a vinylacetate content between 28-40% vinylacetate. In yet other embodiments, the first thermoplastic polymer has a vinylacetate content between 28-33% vinylacetate. In one embodiment, the first thermoplastic polymer has a vinylacetate content of 28%. In one embodiment, the first thermoplastic polymer has a vinylacetate content of 33%.

In some embodiments, the second thermoplastic polymer is an ethylene-vinylacetate copolymer and has a vinylacetate content of 28% or greater. In other embodiments, the second thermoplastic polymer has a vinylacetate content of greater than 28%. In still other embodiments, the second thermoplastic polymer has a vinylacetate content between 28-40% vinylacetate. In yet other embodiments, the second thermoplastic polymer has a vinylacetate content between 28-33% vinylacetate. In one embodiment, the second thermoplastic polymer has a vinylacetate content of 28%. In one embodiment, the second thermoplastic polymer has a vinylacetate content of 33%.

In some embodiments, the second thermoplastic polymer is an ethylene-vinylacetate copolymer and has a vinylacetate content of 28% or less. In other embodiments, the second thermoplastic polymer has a vinylacetate content of less than 28%. In still other embodiments, the second thermoplastic polymer has a vinylacetate content between 9-28% vinylacetate. In yet other embodiments, the second thermoplastic polymer has a vinylacetate content between 9-18% vinylacetate. In one embodiment, the second thermoplastic polymer has a vinylacetate content of 15%. In one embodiment, the second thermoplastic polymer has a vinylacetate content of 18%. It should be noted that when a specific vinylacetate content, e.g., 15%, is mentioned, it refers to the manufacture's target content, and the actual vinylacetate content may vary from the target content by plus or minus 1% or 2%. One of ordinary skill in the art would appreciate that suppliers may use internal analytical methods for determining vinylacetate content, thus there may be an off-set between methods.

The vaginal ring drug delivery system described herein provides a drug delivery system comprising at least two therapeutic agents. In certain embodiments described herein, the first therapeutic agent and the second therapeutic agent are anti-viral agents. Suitable anti-viral agents include anti-HIV agents. An "anti-HIV agent" is any agent which is directly or indirectly effective in the inhibition of HIV reverse transcriptase or another enzyme required for HIV replication or infection, the or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. Suitable anti-viral agents for use in IVR drug delivery systems described herein include, for example, those listed in Table A as follows:

TABLE A

Anti-viral Agents for Preventing HIV infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| Capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| Lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, Isentress ™ | InI |
| (S)-2-(3-chloro-4-fluorobenzyl)-8-ethyl-10-hydroxy-N,6-dimethyl-1,9-dioxo-1,2,6,7,8,9-hexahydropyrazino[1',2':1,5]pyrrolo[2,3-d]pyridazine-4-carboxamide (MK-2048) | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| tipranavir, Aptivus ® | PI |
| Vicriviroc | EI |

EI = entry inhibitor;
FI = fusion inhibitor;
InI = integrase inhibitor; PI = protease inhibitor;
nRTI = nucleoside reverse transcriptase inhibitor;
nnRTI = non-nucleoside reverse transcriptase inhibitor.

Some of the drugs listed in the table can be used in a salt form; e.g., abacavir sulfate, delavirdine mesylate, indinavir sulfate, atazanavir sulfate, nelfinavir mesylate, saquinavir mesylate.

In certain embodiments the anti-viral agents in the vaginal ring drug delivery systems described herein are employed in their conventional dosage ranges and regimens as reported in the art, including, for example, the dosages described in editions of the Physicians' Desk Reference, such as the 63rd edition (2009) and earlier editions. In other embodiments, the anti-viral agents in the vaginal ring drug delivery systems described herein are employed in lower than their conventional dosage ranges.

In certain embodiments, the first therapeutic agent can be an entry inhibitor; fusion inhibitor; integrase inhibitor; protease inhibitor; nucleoside reverse transcriptase inhibitor; or non-nucleoside reverse transcriptase inhibitor.

In certain embodiments, the second therapeutic agent can be an entry inhibitor; fusion inhibitor; integrase inhibitor; protease inhibitor; nucleoside reverse transcriptase inhibitor; or non-nucleoside reverse transcriptase inhibitor.

More specifically, in certain embodiments the first therapeutic agent is an entry inhibitor such as a CCR5 inhibitor. Suitable CCR5 inhibitors include, but are not limited to, maraviroc and vicriviroc.

In certain embodiments the second therapeutic agent is an integrase inhibitor. Suitable integrase inhibitor include, but are not limited to, MK-2048 and raltegravir. MK-2048 is (S)-2-(3-chloro-4-fluorobenzyl)-8-ethyl-10-hydroxy-N,6-dimethyl-1,9-dioxo-1,2,6,7,8,9-hexahydropyrazino[1',2':1,5]pyrrolo[2,3-d]pyridazine-4-carboxamide having the structure:

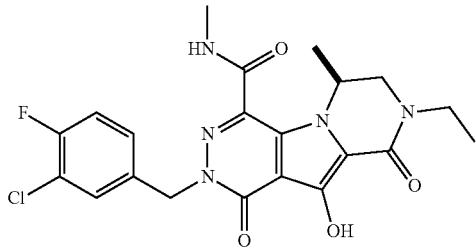 [SMILES: CCN1C[C@H](C)n2c(c(O)c3c(=O)n(Cc4ccc(F)c(Cl)c4)nc(C(=O)NC)c32)C1=O]

In certain embodiments of the vaginal ring drug delivery device described herein, wherein the first therapeutic agent is present in the core about 0.1%-30% by weight. In other embodiments, the first therapeutic agent is present in the core at about 1%-25% by weight, at about 1%-20% by weight, at about 1%-18% by weight or at about 1%-15%% by weight. In other embodiments, the first therapeutic agent is present in the core at about 1%-10% by weight, at about 3%-9% by weight, at about 4%-8% by weight, at about 4%-6%% by weight, or at about 5% by weight. In other embodiments, the first therapeutic agent is present in the core at about 5% by weight, 10% by weight or 20% by weight.

In certain embodiments of the vaginal ring drug delivery device described herein, wherein the first therapeutic agent is vicriviroc, vicriviroc is present in the core about 0.1%-30% by weight. In other embodiments, vicriviroc is present in the core at about 1%-25% by weight, at about 1%-20% by weight, at about 1%-18% by weight or at about 1%-15%% by weight. In other embodiments, vicriviroc is present in the core at about 1%-10% by weight, at about 3%-9% by weight, at about 4%-8% by weight, at about 4%-6%% by weight, or at about 5% by weight. In other embodiments, vicriviroc is present in the core at about 5% by weight, 10% by weight or 20% by weight.

In certain embodiments, the vaginal ring drug delivery systems described herein are capable of releasing the therapeutic agents contained therein over a period of 21, 28 or 31 days. In certain embodiments, the vaginal ring drug delivery systems described herein are capable of releasing the therapeutic agents contained therein over a period of 4, 6, 8 or 12 weeks. In certain embodiments, the vaginal ring drug delivery systems described herein are capable of releasing the therapeutic agents contained therein over a period of one, two or three months.

The vaginal ring described herein, is capable of releasing vicriviroc over a period of 21, 28 or 31 days or 4, 6, 8 or 12 weeks, or one, two or three months at an average rate of between 1-10 mg per day. In certain embodiments, the vaginal ring described herein is capable of releasing vicriviroc at an average rate of between 1-6 mg per day. In certain embodiments, the vaginal ring described herein is capable of releasing vicriviroc over a period of 21, 28 or 31 days at a rate of between 1-4 mg per day. In certain embodiments, the vaginal ring described herein is capable of releasing vicriviroc at an average rate of 1 mg per day. In certain embodiments, the vaginal ring described herein is capable of releasing vicriviroc at an average rate of 2 mg per day. In certain embodiments, the vaginal ring described herein is capable of releasing vicriviroc at an average of 3 mg per day. In certain embodiments, the vaginal ring described herein is capable of releasing vicriviroc at an average of 4 mg per day.

In certain embodiments of the vaginal ring drug delivery device described herein, the second therapeutic agent is present in the skin at about 5-50% by weight. In other embodiments, the second therapeutic agent is present in the skin at about 10-50% by weight, at about 20-50% by weight, at about 10%, 30% or 50% by weight of the skin.

In certain embodiments of the vaginal ring drug delivery device described herein, MK-2048 is present in the in the skin at about 5-50% by weight. In other embodiments, MK-2048 is present in the skin at about 10-50% by weight, at about 20-50% by weight, at about 10%, 30% or 50% by weight of the skin.

The vaginal ring described herein, is capable of releasing MK-2048 over a period of 21, 28 or 31 days or 4, 6, 8 or 12 weeks, or one, two or three months at an average rate of between 0.1-5 mg per day. In certain embodiments, the vaginal ring described herein is capable of releasing MK-2048 at an average rate of between 0.1-3 mg per day. In certain embodiments, the vaginal ring described herein is capable of releasing MK-2048 at a rate of between 0.3-2 mg per day. In certain embodiments, the vaginal ring described herein is capable of releasing MK-2048 at an average rate of between 0.5-2 mg per day.

In certain embodiments, the vaginal ring drug delivery systems described herein are stable at room temperature. As used herein, "room temperature" lies anywhere between about 18° C. and about 30° C. As used herein, a physically stable drug delivery system (ring) is a system which can be stored at about 18° C.–30° C. for at least about one month. In certain embodiments, wherein vicriviroc is in a supersaturated state in the core, the vaginal ring drug delivery systems described herein are stable at room temperature. This is in contrast to the teaching in the prior art. The point of supersaturation of vicriviroc depends on the polymer that vicriviroc is being dissolved in, for example, supersaturation of vicriviroc occurs when vicriviroc is loaded above 1.4% by weight in EVA 28.

Physical stability is related to delayed re-crystallization of dissolved drug present in the super saturated state in either the interior of the system or on the surface of the system or both in interior and on the surface. Delayed re-crystallization on the surface will result in an increase of the on-set release measured under sink conditions after 24 hours. Delayed crystallization in the interior of the ring will result in the opposite effect namely a decrease of the entire release profile. If delayed crystallization is occurring both on the surface and in the interior of the system, likely an increase of the on-set release at day-1 will be observed whereas a decrease of the release after day-1 will be observed. Physical stability is defined as constant in-vitro release profiles obtained during long-term storage at room temperature with an increase of day 1 release that is either absent or levels off. Some initial minor changes occurring within 1 month when stored at room temperature are not considered to be related to physical instability. These small changes can be related to transient internal diffusion phenomena which will automatically come to a halt when drug distribution is in equilibrium.

The vaginal ring drug delivery systems described herein are primarily designed for prevention of transmission of HIV. Described herein are methods of prevention of HIV transmission which comprise the steps of positioning the vaginal ring drug delivery systems described herein within a female vaginal tract and retaining the system within the vaginal tract for at least approximately 21 days.

Also described herein are methods of preventing HIV which comprises the steps of positioning the vaginal ring drug delivery systems described herein within the female vaginal tract and retaining the system within the vaginal tract for at least approximately 21 days.

Also described herein is a use of a vaginal ring drug delivery system described herein for the manufacture of a HIV prevention kit.

Also described herein is a use of a vaginal ring drug delivery system described herein for the manufacture of a preparation to and/or prevent a sexually transmitted disease such as for example AIDS.

Also described herein are methods of treating HIV which comprises the steps of positioning the vaginal ring drug delivery systems described herein within the female vaginal tract and retaining the system within the vaginal tract for at least approximately 21 days.

Also described herein is a use of a vaginal ring drug delivery system described herein for the manufacture of a HIV treatment kit.

Also described herein is a use of a vaginal ring drug delivery system described herein for the manufacture of a treatment of a sexually transmitted disease such as for example AIDS.

Also described herein are methods of manufacturing the vaginal ring drug delivery systems described herein comprising:
(i) producing a homogenous polymer core granulate comprising the first therapeutic agent and a loaded skin layer granulate comprising the second therapeutic agent;
(ii) co-extruding the core granulate comprising the first therapeutic agent and the skin layer granulate comprising the second therapeutic agent to form two-layered drug delivery system or coextruding the core granulate comprising the first therapeutic agent with additional core layers and/or the skin granulate comprising the second therapeutic agent with additional skin layers to form a multi-layered drug delivery system.

Also described herein are methods of manufacturing the drug loaded core or skin granulate:
(a) grinding the polymer;
(b) dry powder mixing the ground polymer with the respective active compound
(c) blend extruding the resulting powder mixtures of step (b)
(d) cutting the resulting loaded polymer strands into granules, thereby obtaining a core granulate and/or the skin layer granulate; and
(e) when required lubricating the granulate prior to coextrusion.

Additionally, described herein are the vaginal ring drug delivery systems comprising a first and second therapeutic agent that further comprise at least one contraception agent, such as a steroid. More specifically, in certain embodiments the steroid is a progestogenic steroidal compound. Suitable progestogens include, but are not limited to, nomegestrol acetate (NOMAc), natural progesterone, dydrogesterone, medrogestone, medroxyprogesterone acetate, megestrol acetate, chlormadinone acetate, cyproterone acetate, gestonorone caproate, demegestone, promegestone, nestorone, trimegestone, Norethisterone (=norethindrone), norethisterone acetate, lynestrenol, ethinodiol acetate, norethinodrel, norgestrel, norgestimate, dienogest, etonogestrel, levonorgestrel, drospirenone, or any other suitable steroidal compound with progestogenic activity.

In certain embodiments the steroid is an estrogenic steroidal compound. Suitable estrogens include, but are not limited to, 17beta-estradiol, 17beta-estradiol hemi-hydrate, estriol, mestranol and ethinyl estradiol.

Depending on the steroid, the steroid can be in dissolved or solid form. Solid form may be crystalline or amorphous. Additionally, depending on the steroid and the release rate desired, the steroid can be loaded in the skin or the core. In certain embodiments, the steroid can be loaded in the skin. In other embodiments, the steroid can be loaded in a layer of the skin wherein the skin is comprised of two or more layers. In certain embodiments, the steroid can be loaded in the core.

In other embodiments, the steroid will be loaded in a layer of the core wherein the core is comprised of two or more layers.

In certain embodiments wherein the steroid is etonogestrel, the etonogestrel is dissolved in the core or a layer of the core of the vaginal ring drug delivery systems described herein. In certain embodiments, the etonogestrel is present in the core at about 0.10%-1.0% by weight. In other embodiments, etonogestrel is present in the core at about 0.15-0.70% by weight, at about 0.20-0.60% by weight, at about 0.25-0.60% by weight, at about 0.25-0.50% by weight, or at about 0.15%, or 0.20 or 0.25% by weight.

In certain embodiments wherein the steroid is 17beta-estradiol or 17beta-estradiol hemi-hydrate, the 17beta-estradiol or 17beta-estradiol hemi-hydrate is dissolved in the core or a layer of the core of the vaginal ring drug delivery systems described herein. In certain embodiments of the vaginal ring drug delivery systems described herein, 17beta-estradiol or 17beta-estradiol hemi-hydrate is present in the core at about 0.10%-1.0% by weight. In other embodiments, 17beta-estradiol or 17beta-estradiol hemi-hydrate is present in the core at about 0.15-0.70% by weight, at about 0.20-0.60% by weight, at about 0.25-0.60% by weight, at about 0.25-0.50% by weight, or at about 0.20%, or 0.30 or 0.40% by weight.

In certain embodiments wherein the steroid is nomegestrol acetate, the nomegestrol acetate is loaded in the core. In certain embodiments wherein the steroid is nomegestrol acetate, the nomegestrol acetate is loaded in a layer of the core, wherein the core comprises two or more layers. In certain embodiments, nomegestrol acetate is loaded in the vaginal ring drug delivery devices described herein in solid form. In certain embodiments of the vaginal ring drug delivery systems described herein, nomegestrol acetate is present in crystalline form at about 1%-40% by weight. In other embodiments, nomegestrol acetate is present in crystalline form at about 10-40% by weight, at about 10-30% by weight, at about 15-30% by weight, at about 20-30% by weight, or at about 20%, or 25% or 28% by weight.

Examples of embodiments are further described in the following examples which are not in any way intended to limit the scope of the invention as claimed.

EXAMPLES

Example 1

Manufacturing of Vaginal Ring Drug Delivery Systems Containing Anti-Viral Agents Mixing Therapeutic Agents Through the Copolymers EVA15 and EVA28

Vicriviroc (VCV) or MK-2048 were homogeneously mixed through polymer. The mixing was performed in two steps. In the first step, dry powder mixing was performed with the therapeutic agents and polymer powder in a stainless steel drum using a Rhönrad (Barrel-hoop principle) for 60 minutes. Subsequently the homogenized powder mixtures were blend extruded using a 25 mm co-rotating double screw blend extruder (Berstorff ZE25) at a temperature of 90° C. and the resulting medicated polymer strands were cut into granules using a Scheer granulator. The compositions for the various mixtures are listed in Table 1. After granulation these batches were transferred to the next processing step (co-extrusion) proceeded by a lubrication step when applicable.

TABLE 1

| Granulate with only anti-viral agents | | | |
|---|---|---|---|
| Granulate batch | VCV drug load | MK-2048 drug load | EVA polymer |
| A | 5 wt % | N/A | EVA 28 |
| B | 10 wt % | N/A | EVA 28 |
| C | N/A | 30 wt % | EVA 15 |
| D | N/A | 40 wt % | EVA 15 |
| E | 20 wt % | N/A | EVA 28 |
| F | N/A | 50 wt % | EVA 15 |
| G | N/A | 30 wt % | EVA 28 |
| H | N/A | 20 wt % | EVA 28 |

Co-Extrusion and Ring Welding

The granulates of batches A-D containing the therapeutic agents were further processed into drug-loaded fibers by means of co-extrusion using a FOURNE co-extruder. This co-extrusion set-up consisted of two or three coupled single screw extruders. The extruders, equipped with separate spinning pumps to control the volume flow rates, were connected with an extruder die in which the melt flows are combined to form a two- or three-layered fiber. All fibers were extruded at an extrusion temperature of 100° C. Each of the fiber variants were produced by using the appropriate spinning rate and spinning pump settings. The outer diameter of the fiber was measured on-line continuously using a laser micrometer and recorded. The thickness of the layers was controlled by means of the spinning pump settings. Target diameter was approximately 4 mm.

The composition of different series of fiber batches produced are given in Table 2:

TABLE 2

| Composition of fiber batches | | |
|---|---|---|
| Nos. | Core material | Skin material/ thickness |
| 1 | A | C/50 μm |
| 2 | B | C/50 μm |
| 3 | B | D/50 μm |
| 4 | A | EVA 28/50 μm |
| 5 | EVA 28 | G/50 μm |
| 6 | EVA 28 | H/50 μm |
| 7 | A | G/50 μm |
| 8 | A | H/50 μm |
| 9 | B | G/50 μm |
| 10 | B | EVA 28/50 μm |

All fiber batches were cut to a target length of 157±1 mm and welded into rings using welding molds at a welding temperature of approximately 130° C.

Example 2

In Vitro Release of Vaginal Rings

Figure 2:
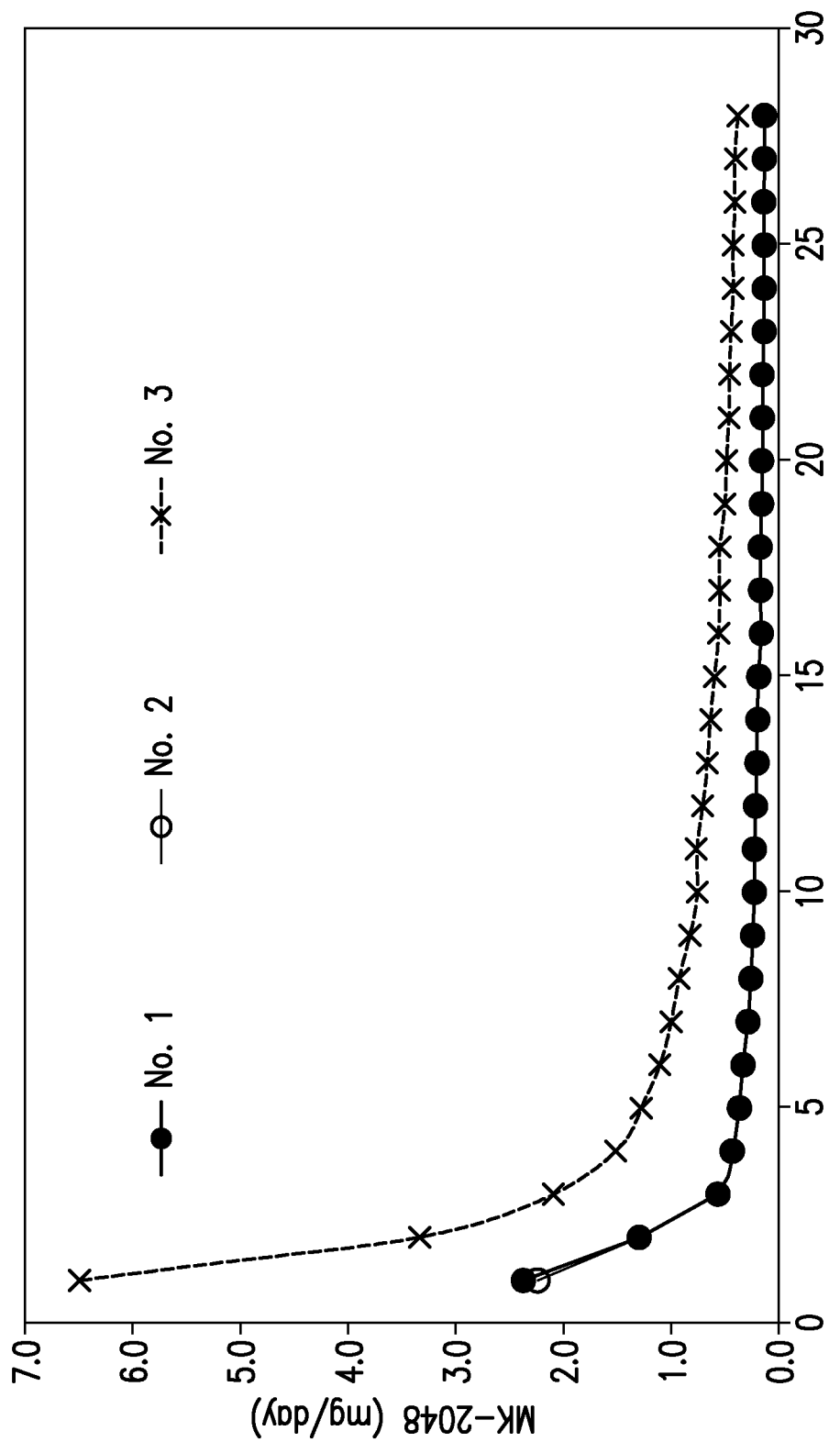
FIG. 2 show the in vitro release of MK-2048 from vaginal ring drug delivery systems exemplified herein.
Figure 3:
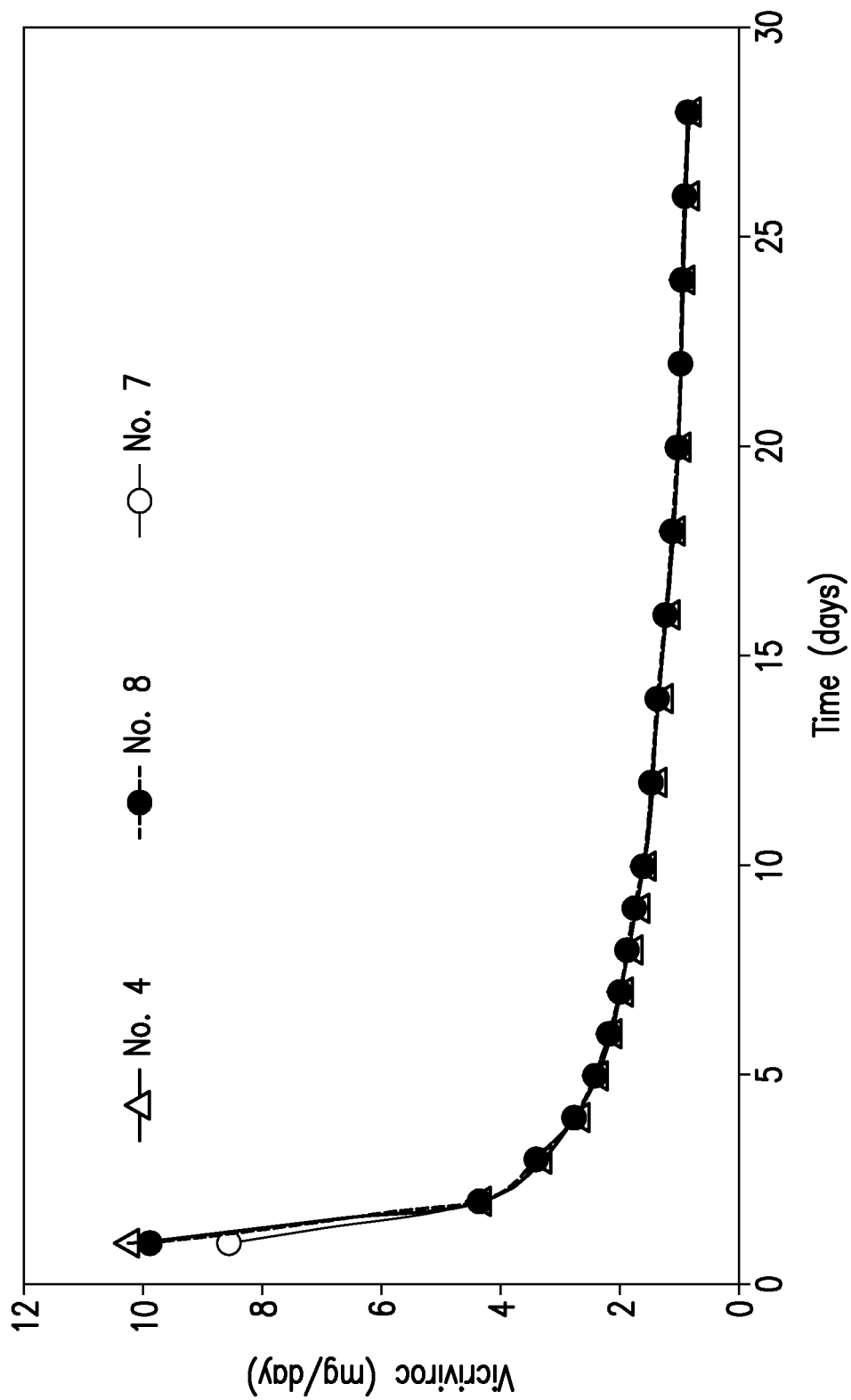
FIG. 3 show the in vitro release of vicriviroc from vaginal ring drug delivery systems exemplified herein.
Figure 4:
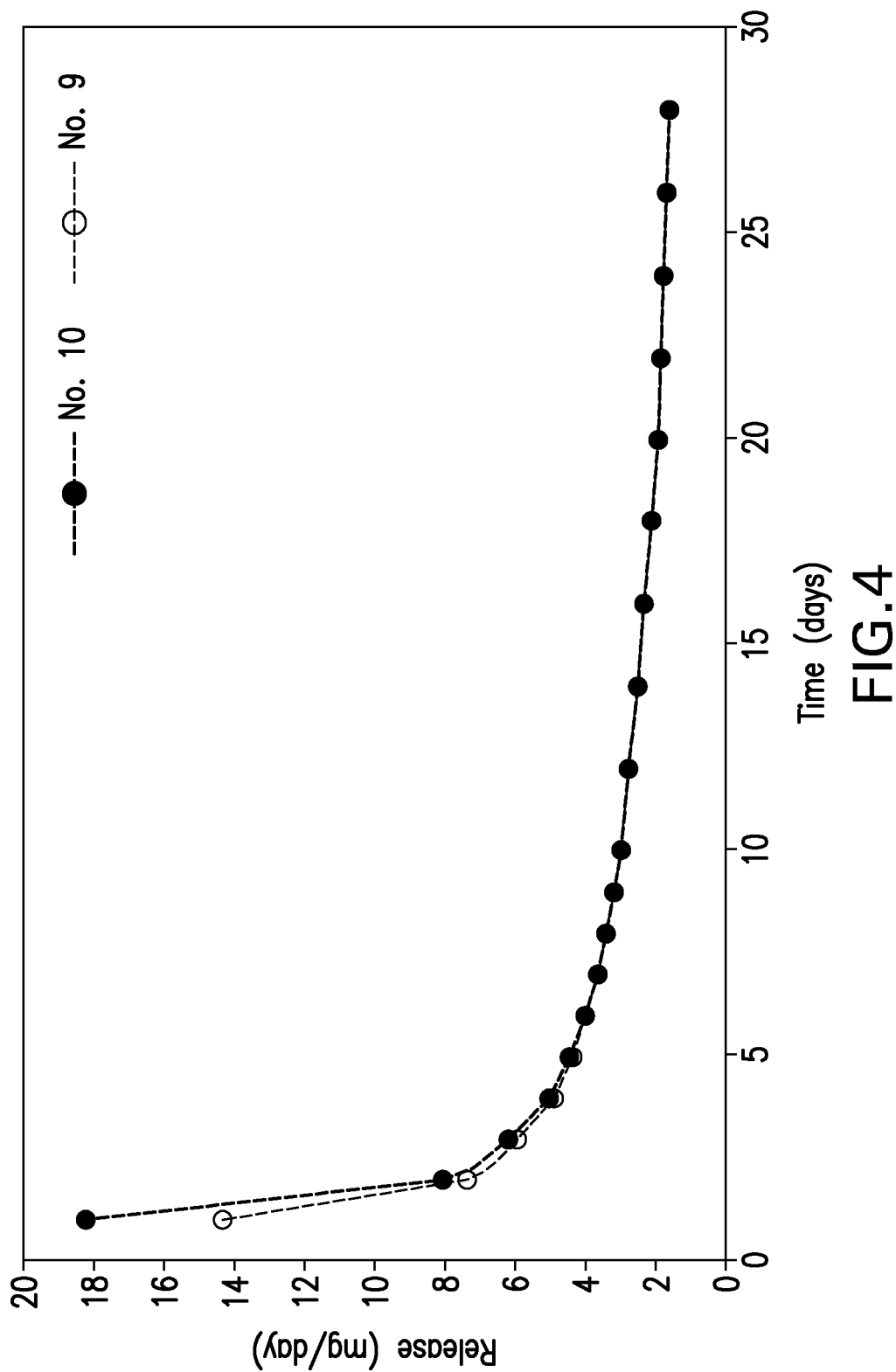
FIG. 4 show the in vitro release of vicriviroc from vaginal ring drug delivery systems exemplified herein.
Figure 5:
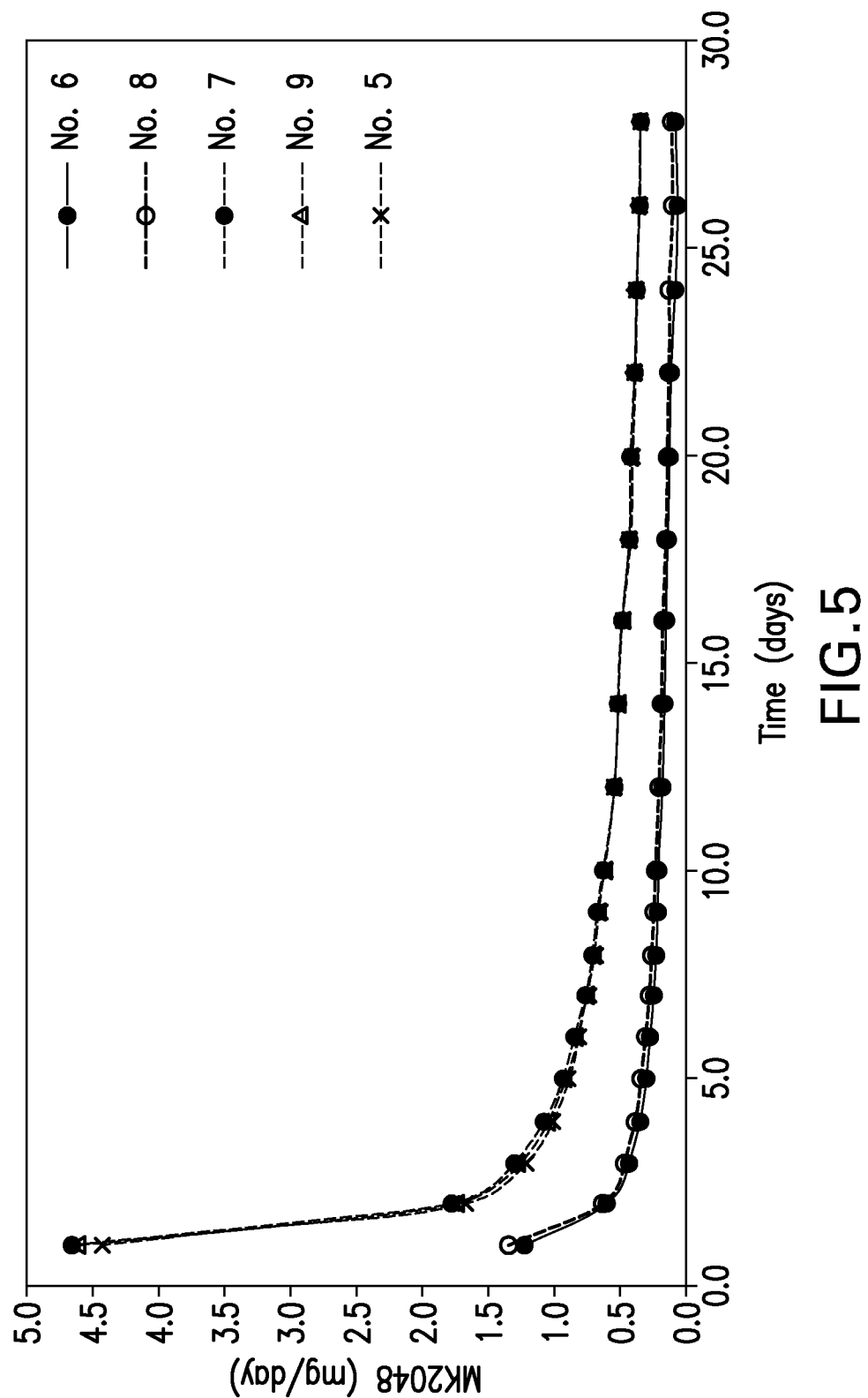
FIG. 5 show the in vitro release of MK-2048 from vaginal ring drug delivery systems exemplified herein.

The in-vitro release rate was determined in 100 ml purified water containing 1% sodium dodecyl sulfate (SDS) to maintain sink conditions. The rings were incubated in the continuously stirred in-vitro release medium which was maintained at 37±0.2° C. and refreshed every 24 hours. Detection of the active ingredients in the in-vitro release medium was performed with HPLC. FIG. 1 shows the in vitro release of vicriviroc of ring nos. 1, 2 and 3. FIG. 2 show the in vitro release of MK-2048 of ring nos. 1, 2 and 3. FIG. 3 shows the in vitro release of vicriviroc of ring nos. 4, 8 and 7. FIG. 4 shows the in vitro release of viriviroc of ring nos. 9 and 10. FIG. 5 shows the in vitro release of MK-2048 of ring nos. 5, 6, 7, 8 and 9.

Example 3

Manufacturing of Vaginal Rings Containing Anti-Retroviral Agents and Contraceptive Agents Mixing Therapeutic Agents Through the Copolymers EVA28

Each therapeutic agent for each granulate batch listed in Table 3 below were homogeneously mixed through the polymer. Mixing was performed in two steps. In the first step, dry powder mixing was performed with the therapeutic agents and polymer powder in a stainless steel drum using a Rhönrad (Barrel-hoop principle) for 60 minutes. Subsequently the homogenized powder mixtures were blend extruded using a 25 mm co-rotating double screw blend extruder (Berstorff ZE25) at a temperature of approximately 95° C. and the resulting medicated polymer strands were cut into granules using a Scheer granulator. After granulation these batches were transferred to the next processing step (co-extrusion) proceeded by a lubrication step when applicable.

TABLE 3

| Granulate containing contraceptive agents | | | | | |
|---|---|---|---|---|---|
| Granulate batch | VCV drug load | ENG drug load | E2 drug load | Nomac drug load | EVA polymer |
| J | 20 wt % | 0.25 wt % | n/a | n/a | EVA 28 |
| K | 20 wt % | 0.25 wt % | 0.4 wt % | n/a | EVA 28 |

TABLE 3-continued

Granulate containing contraceptive agents

| Granulate batch | VCV drug load | ENG drug load | E2 drug load | Nomac drug load | EVA polymer |
|---|---|---|---|---|---|
| L | 20 wt % | n/a | 0.4 wt % | n/a | EVA 28 |
| M | n/a | n/a | n/a | 28 wt % | EVA 28 |

Co-Extrusion and Ring Welding

Granulates containing the therapeutic agents were further processed to drug loaded fibers by means of co-extrusion using a Fourne co-extruder. This co-extrusion set-up consisted of three coupled single screw extruders. The extruders, equipped with separate spinning pumps to control the volume flow rates, were connected with an extruder die in which the melt flows are combined to form a three-layered fiber. All fibers were extruded at an extrusion temperature of approximately 90° C. Each of the fiber variants were produced by using the appropriate spinning rate and spinning pump settings. The outer diameter of the fiber was measured on-line continuously using a laser micrometer and recorded. Target diameter is approximately 4 mm. The thickness of the layers was controlled by means of the spinning pump settings.

TABLE 4

| Nos. | First layer Core material | Second layer Core/ thickness | Skin first layer material/thickness | Skin second layer material/thickness |
|---|---|---|---|---|
| 11 | E | M/60 μm | N/A | D/122 μm |
| 12 | L | M/60 μm | N/A | D/122 μm |
| 13 | K | N/A | EVA 15/200 μm | D/50 μm |
| 14 | J | N/A | EVA 15/200 μm | D/50 μm |

Example 5

In Vitro Release of Vaginal Rings

Figure 6:
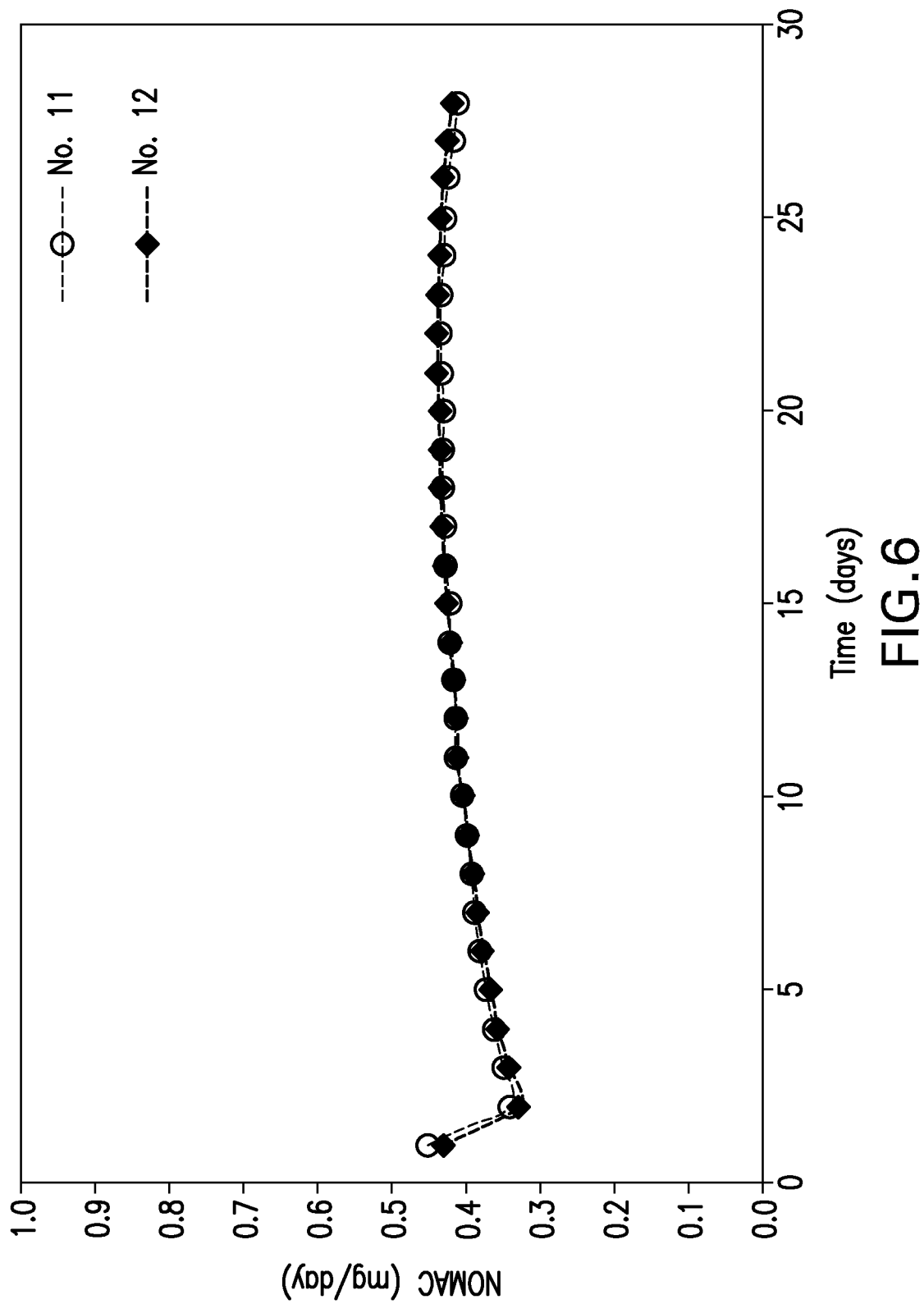
FIG. 6 shows the in-vitro release of NOMAC from vaginal ring drug delivery systems exemplified herein.
Figure 7:
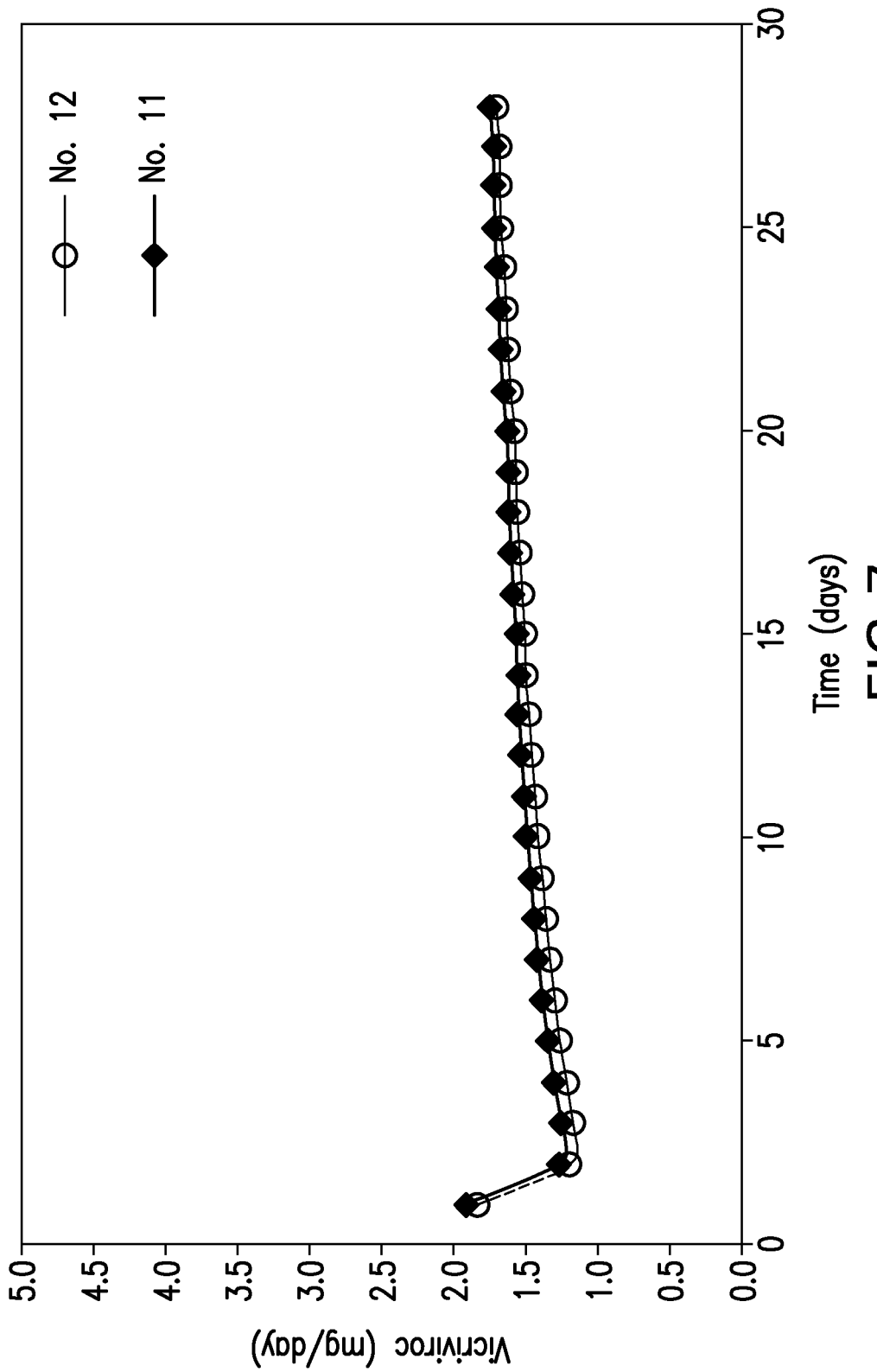
FIG. 7 shows the in-vitro release of vicriviroc from vaginal ring drug delivery systems exemplified herein.
Figure 8:
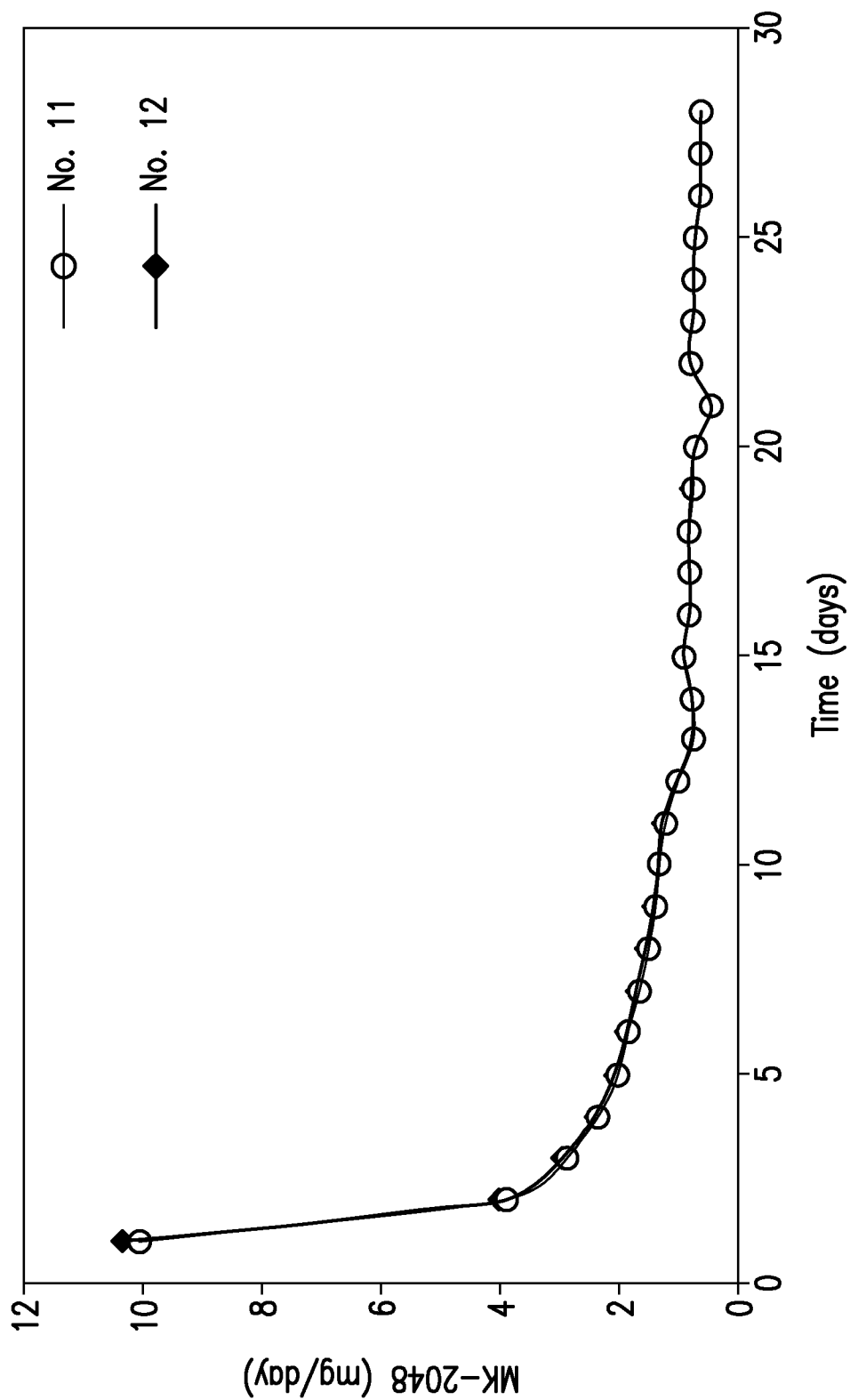
FIG. 8 shows the in-vitro release of MK-2048 from vaginal ring drug delivery systems exemplified herein.
Figure 9:
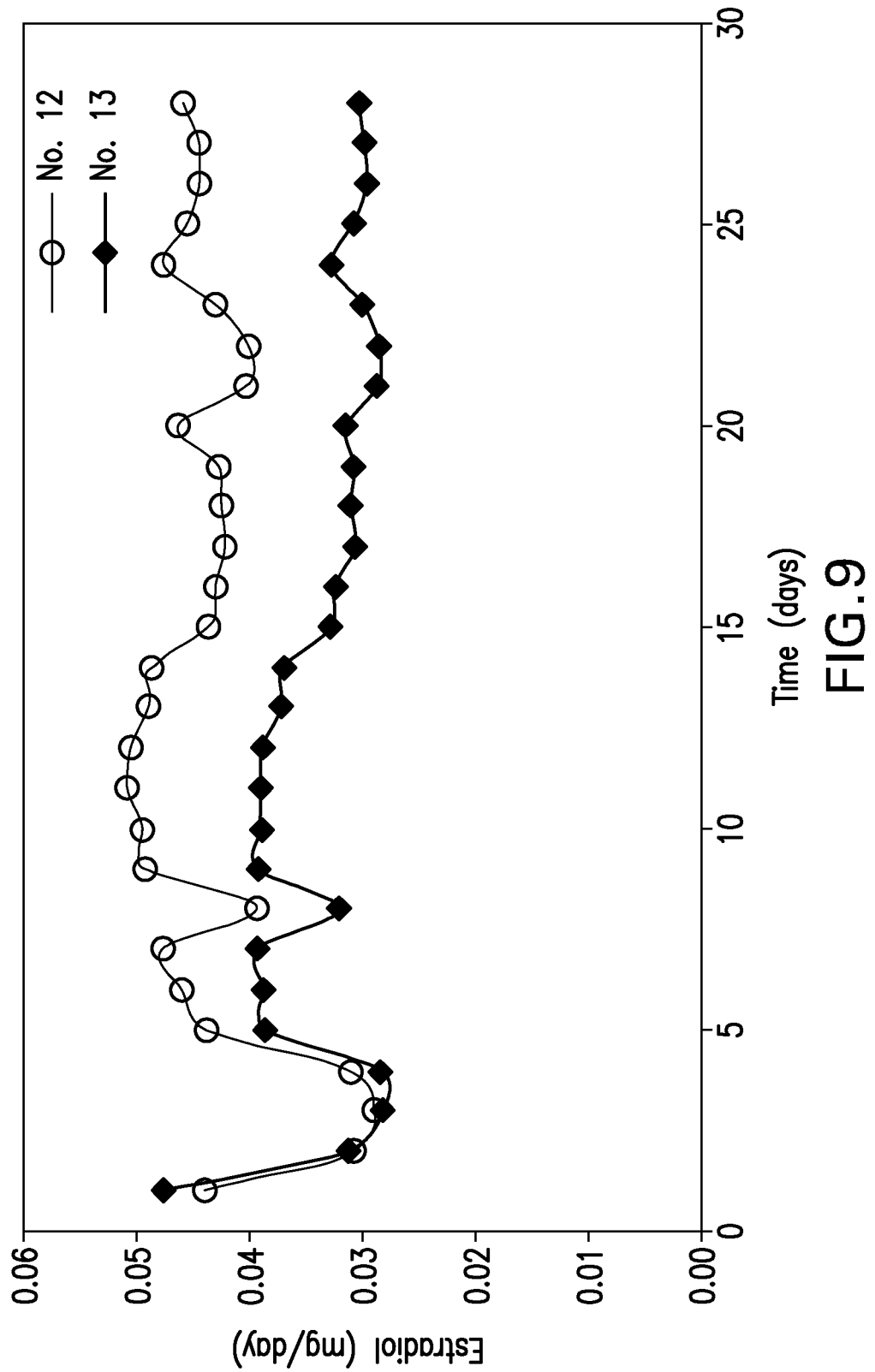
FIG. 9 shows the in-vitro release of estradiol from vaginal ring drug delivery systems exemplified herein.
Figure 10:
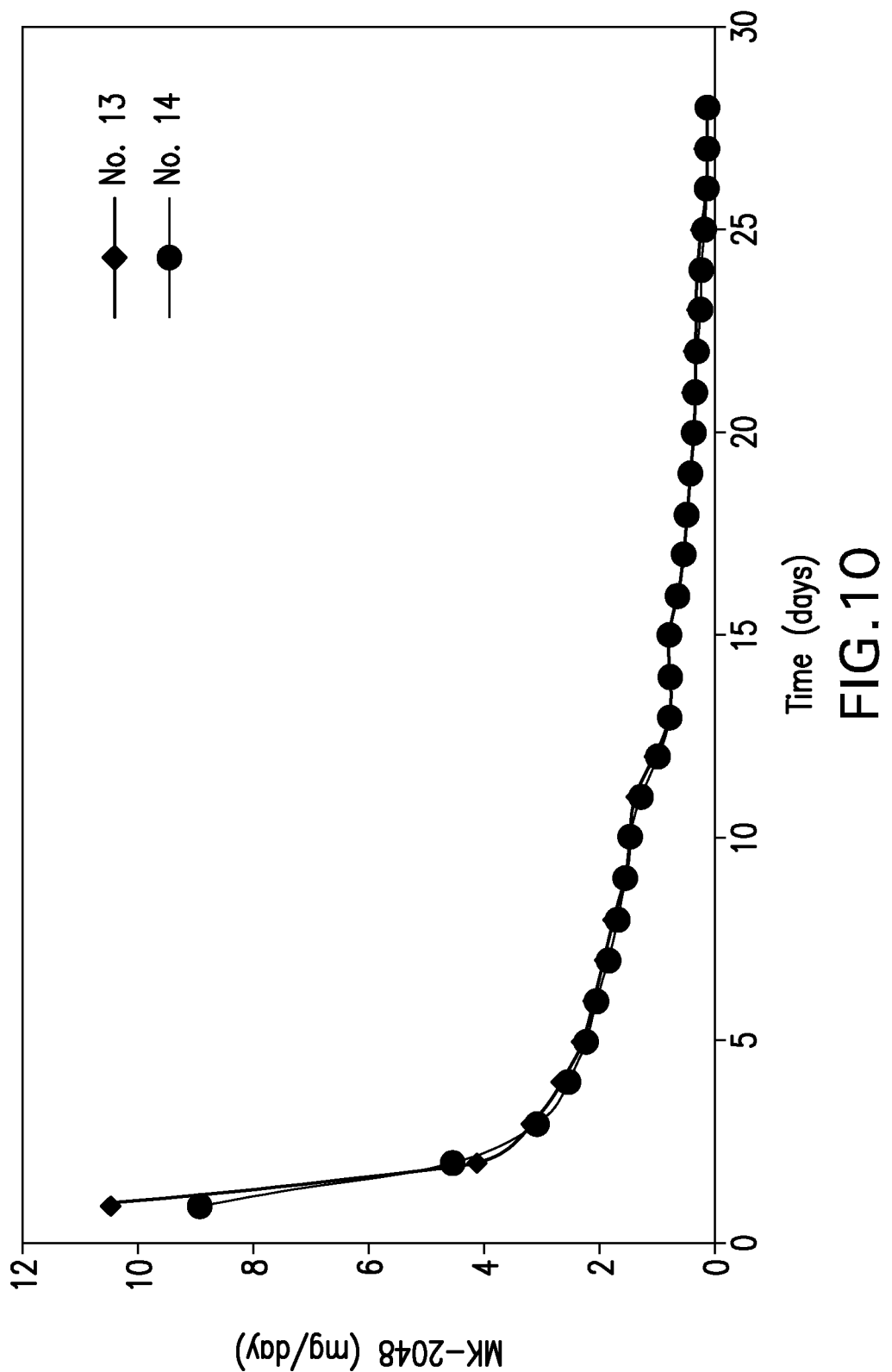
FIG. 10 shows the in-vitro release of MK-2048 from vaginal ring drug delivery systems exemplified herein.
Figure 11:
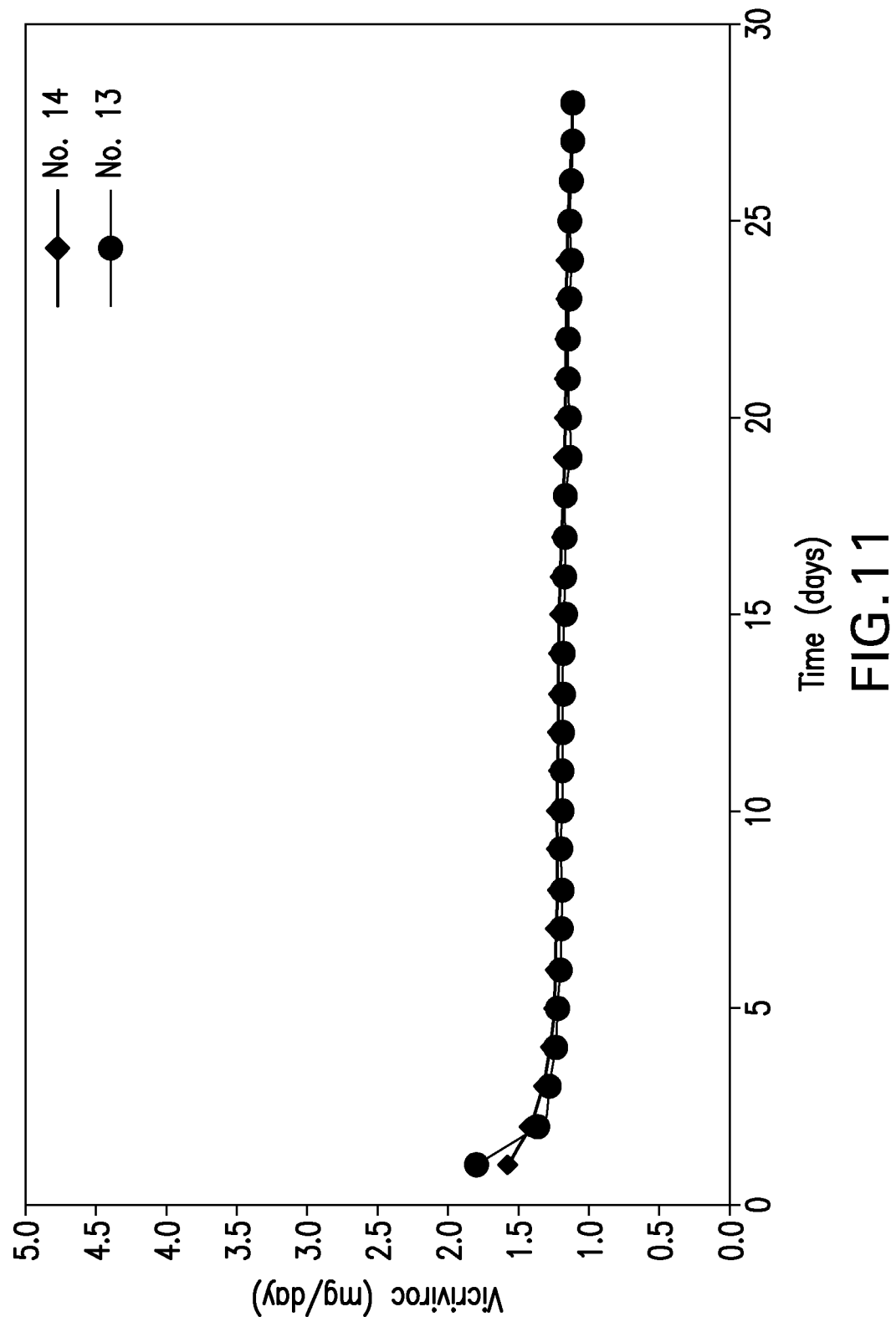
FIG. 11 shows the in-vitro release of vicriviroc from vaginal ring drug delivery systems exemplified herein.
Figure 12:
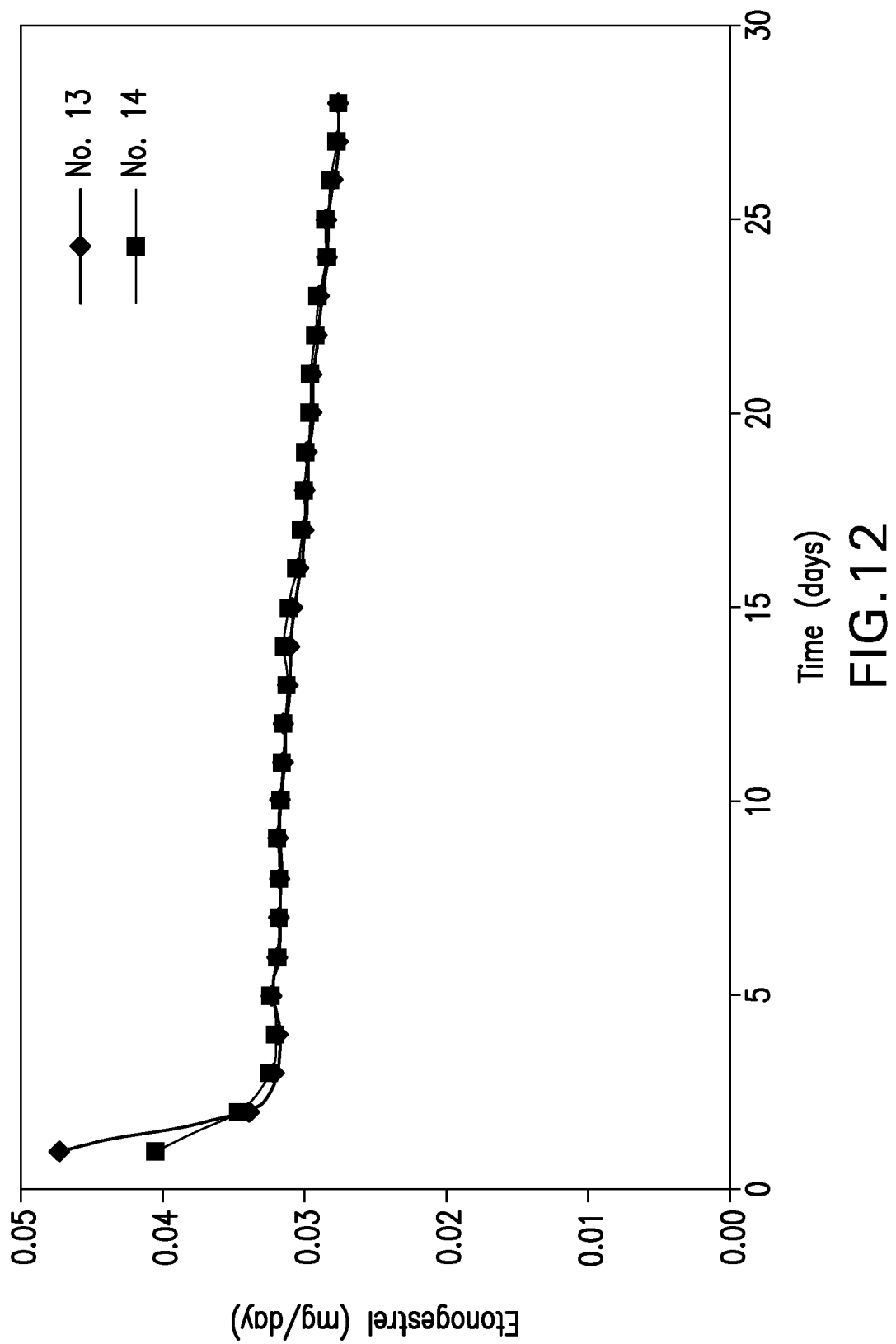
FIG. 12 shows the in-vitro release of etonogestrel from vaginal ring drug delivery systems exemplified herein.
Figure 13:
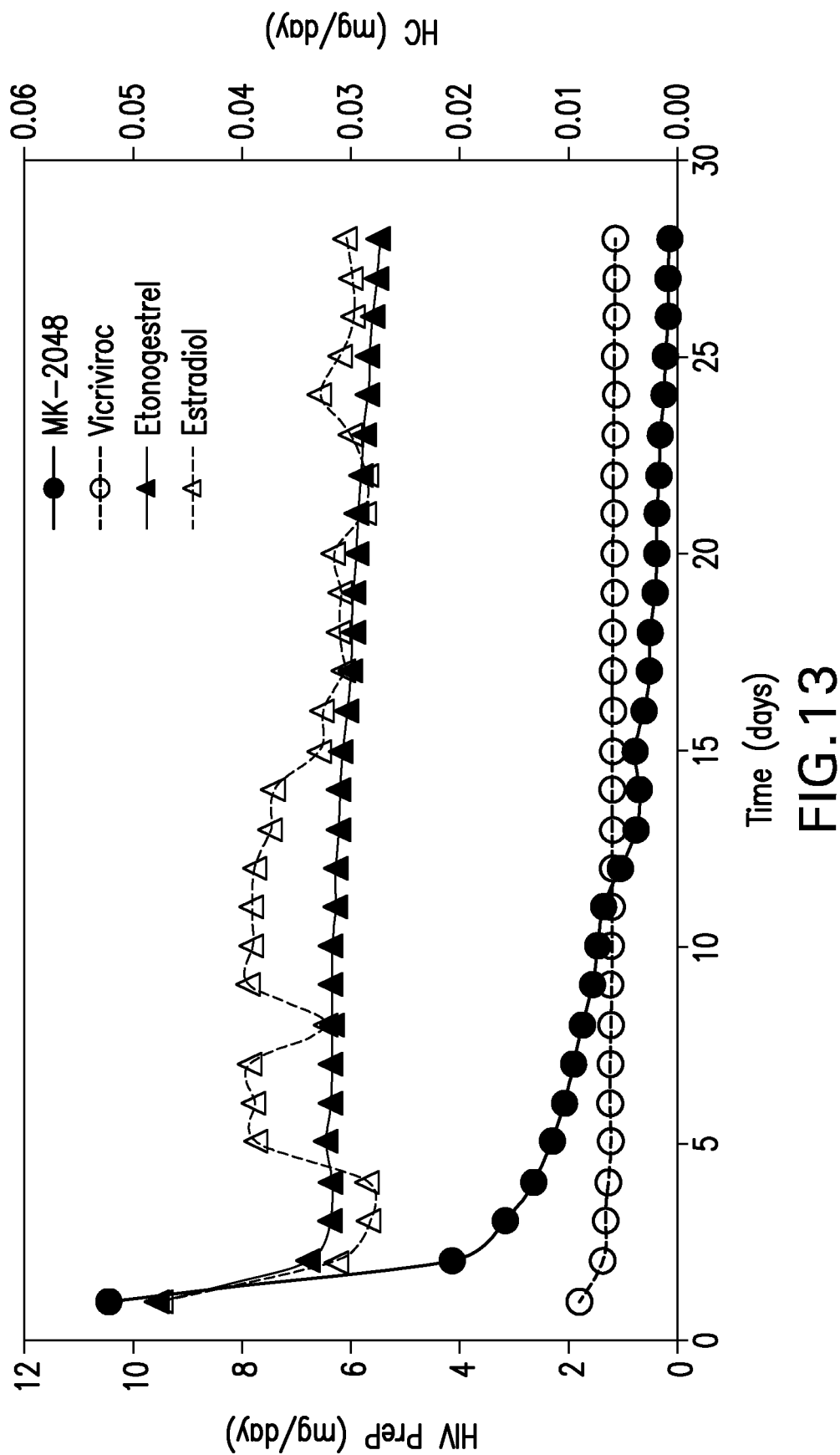
FIG. 13 shows the release of MK-2048, vicriviroc, etonogestrel and estradiol from vaginal ring drug delivery systems exemplified herein.

The in-vitro release rate of ring nos. 11, 12, 13 and 14 are shown in FIGS. 6-13. The in-vitro release rate was determined in 100 ml 50 mM acetate buffer containing 1% sodium dodecyl sulfate (SDS) to maintain sink conditions. The rings were incubated in the continuously stirred in-vitro release medium which was maintained at 37±0.2° C. and refreshed every 24 hours. Detection of the active ingredients in the in-vitro release medium was performed with HPLC-UV. FIG. 6 shows the in-vitro release of NOMAC of ring nos. 11 and 12. FIG. 7 shows the in-vitro release of vicriviroc of ring nos. 11 and 12. FIG. 8 shows the in-vitro release of MK-2048 of ring nos. 11 and 12. FIG. 9 shows the in-vitro release of estradiol of ring nos. 12 and 13. FIG. 10 shows the in-vitro release of MK-2048 of ring nos. 13 and 14. FIG. 11 shows the in-vitro release of vicriviroc of ring nos. 13 and 14. FIG. 12 shows the in-vitro release of etonogestrel of ring nos. 13 and 14. FIG. 13 shows the release of MK-2048, vicriviroc, etonogestrel and estradiol of ring no. 13.

Example 6

Vicriviroc Solubility as a Function of Vinylacetate Content

The solubility of vicriviroc in EVA was determined by partitioning experiments. A small sample of polymer film (approximately 10 mg) was immersed in a saturated aqueous vicriviroc solution (5 mL PBS buffer pH 7). Once the film was immersed the drug diffused from the saturated solution into the film until an equilibrium was achieved. As a result the drug concentration of the aqueous solution decreased and the drug concentration in the film increased. The decrease of the drug concentration in the aqueous solution was continuously measured with a fiber optic probe (Rainbow Dynamic Dissolution Monitor).

Figure 14:
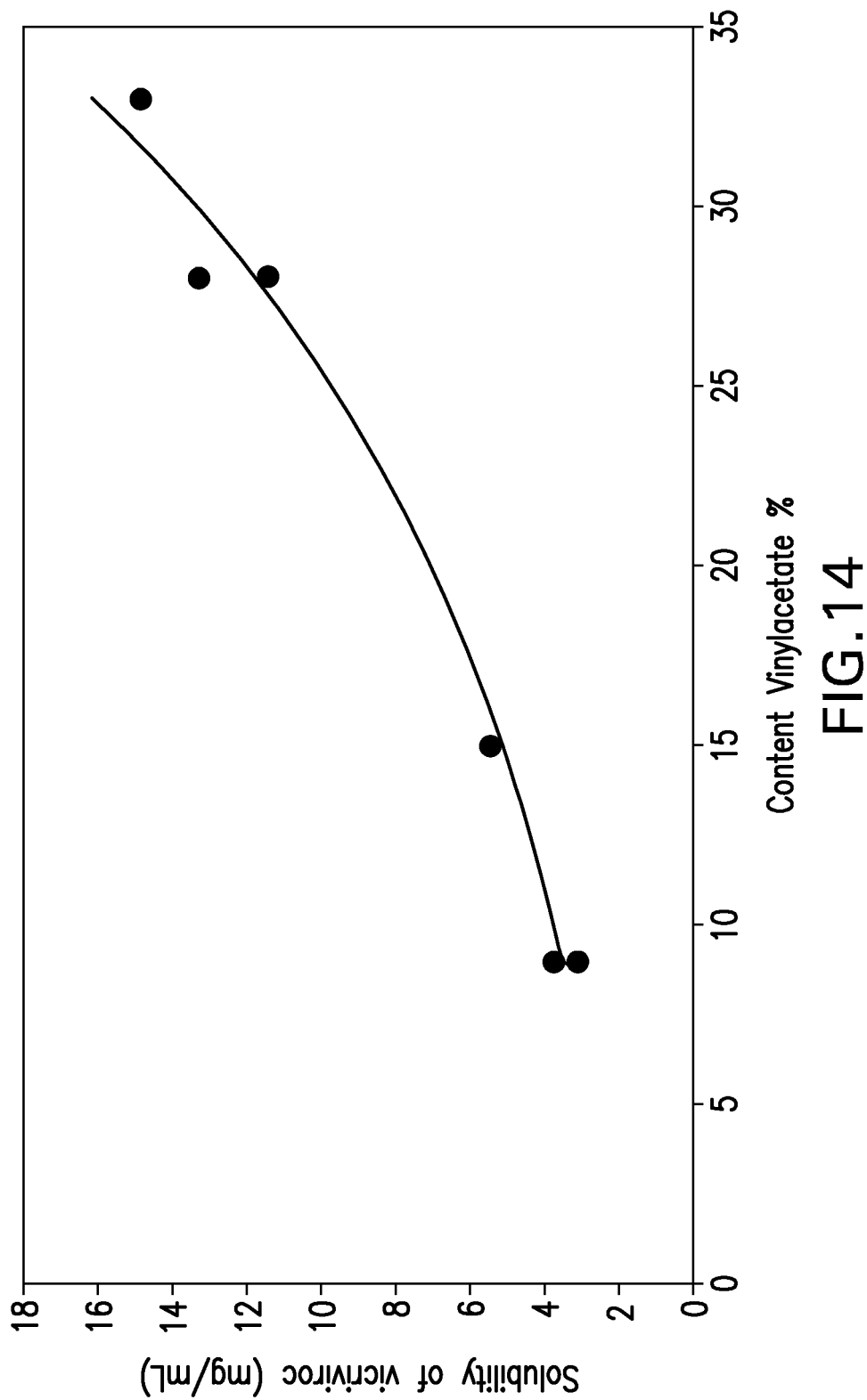
FIG. 14 shows the solubility of vicriviroc in EVA28.

Solubility of vicriviroc in EVA 28 has been determined and is approximately 1.2-1.4 wt % as can be seen in FIG. 14. The coextruded rings contained up to 20 wt % vicriviroc in EVA 28 where the vicriviroc is completely dissolved while maintaining a stable in vitro release profile during storage.

Example 7

Stability

Figure 15:
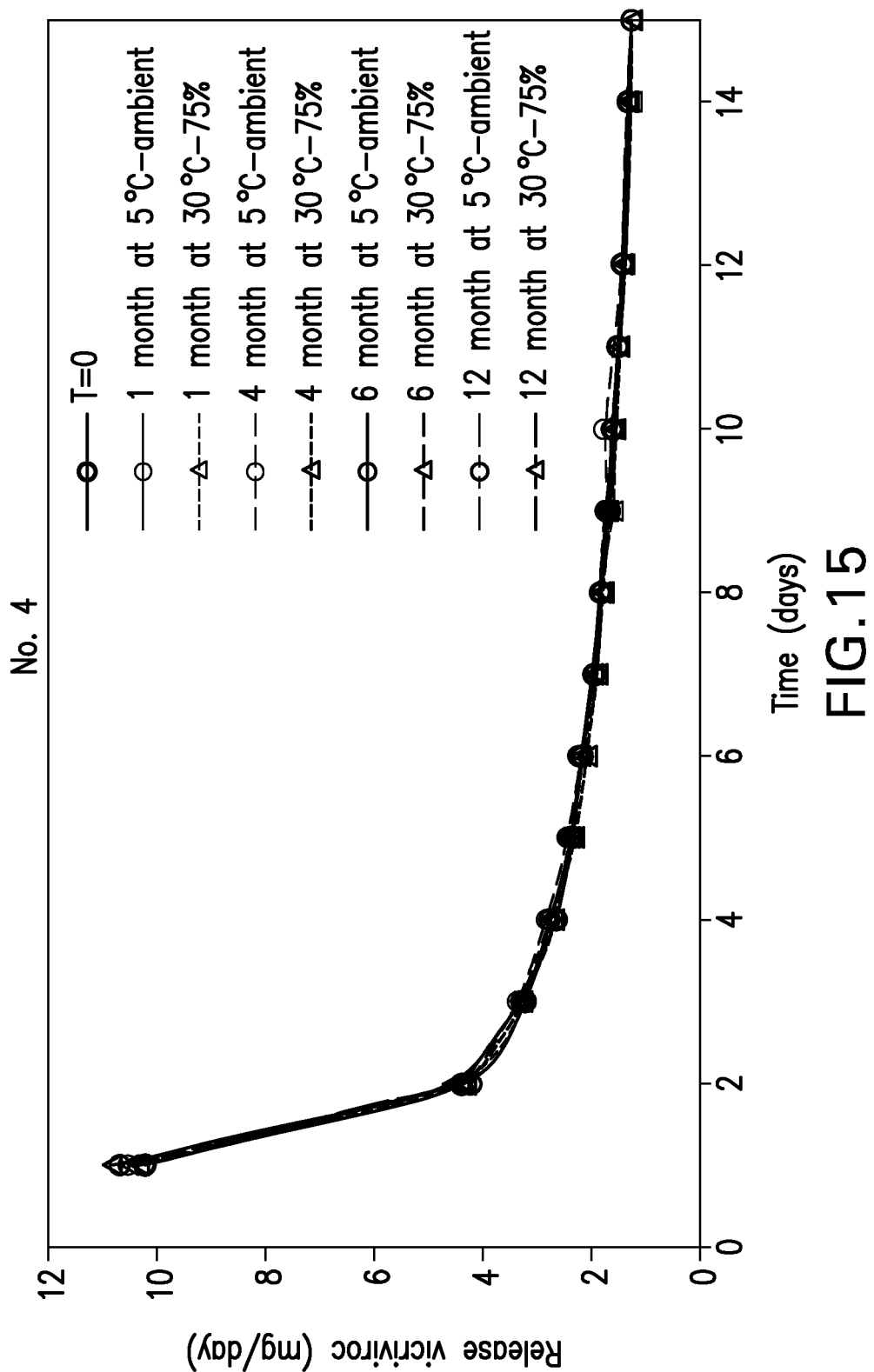
FIG. 15 shows the in vitro release of vicriviroc from vaginal ring drug delivery systems exemplified herein up to 12 months storage at 30° C.
Figure 16:
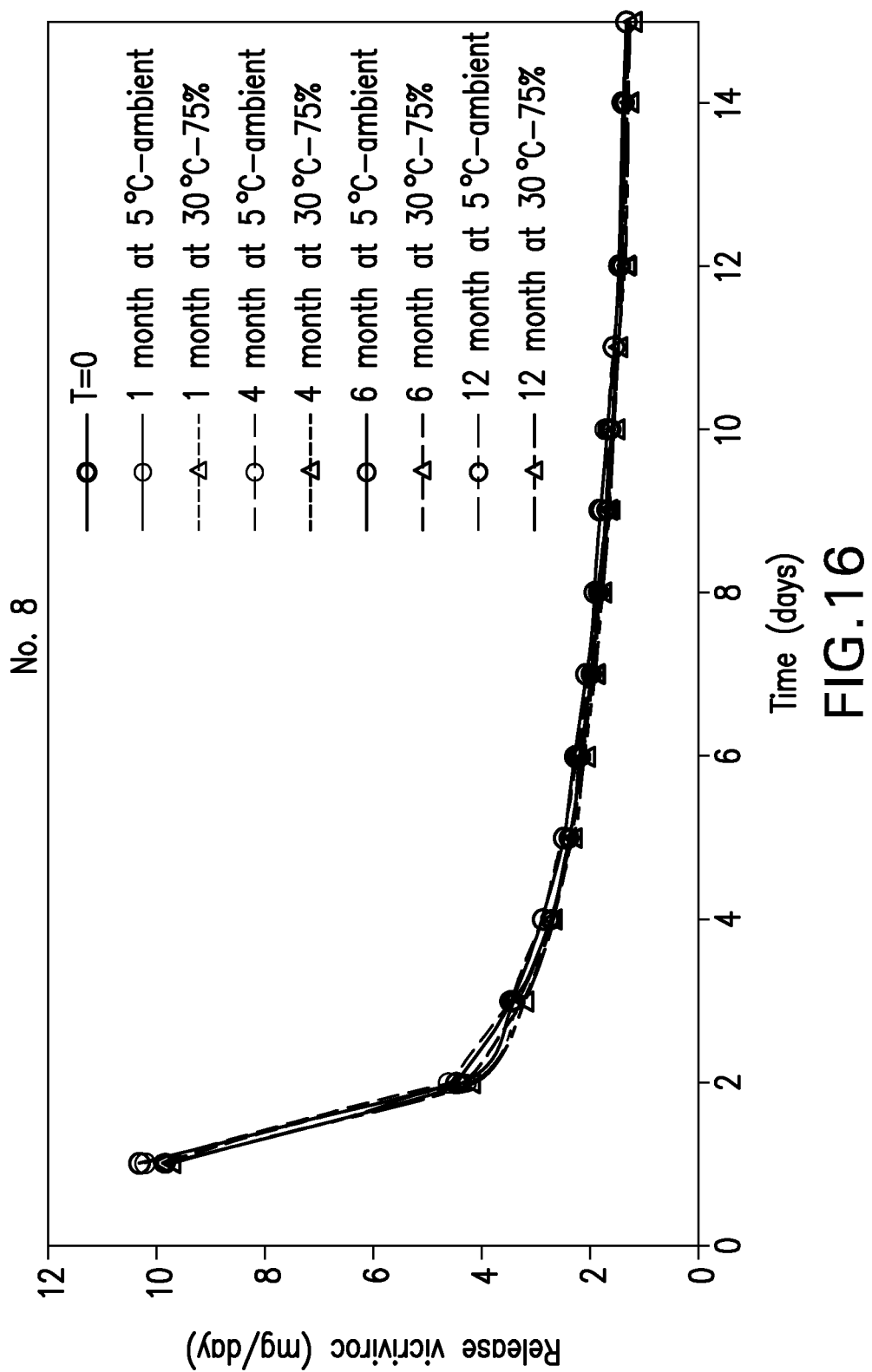
FIG. 16 shows the in vitro release of vicriviroc from vaginal ring drug delivery systems exemplified herein up to 12 months storage at 30° C.
Figure 17:
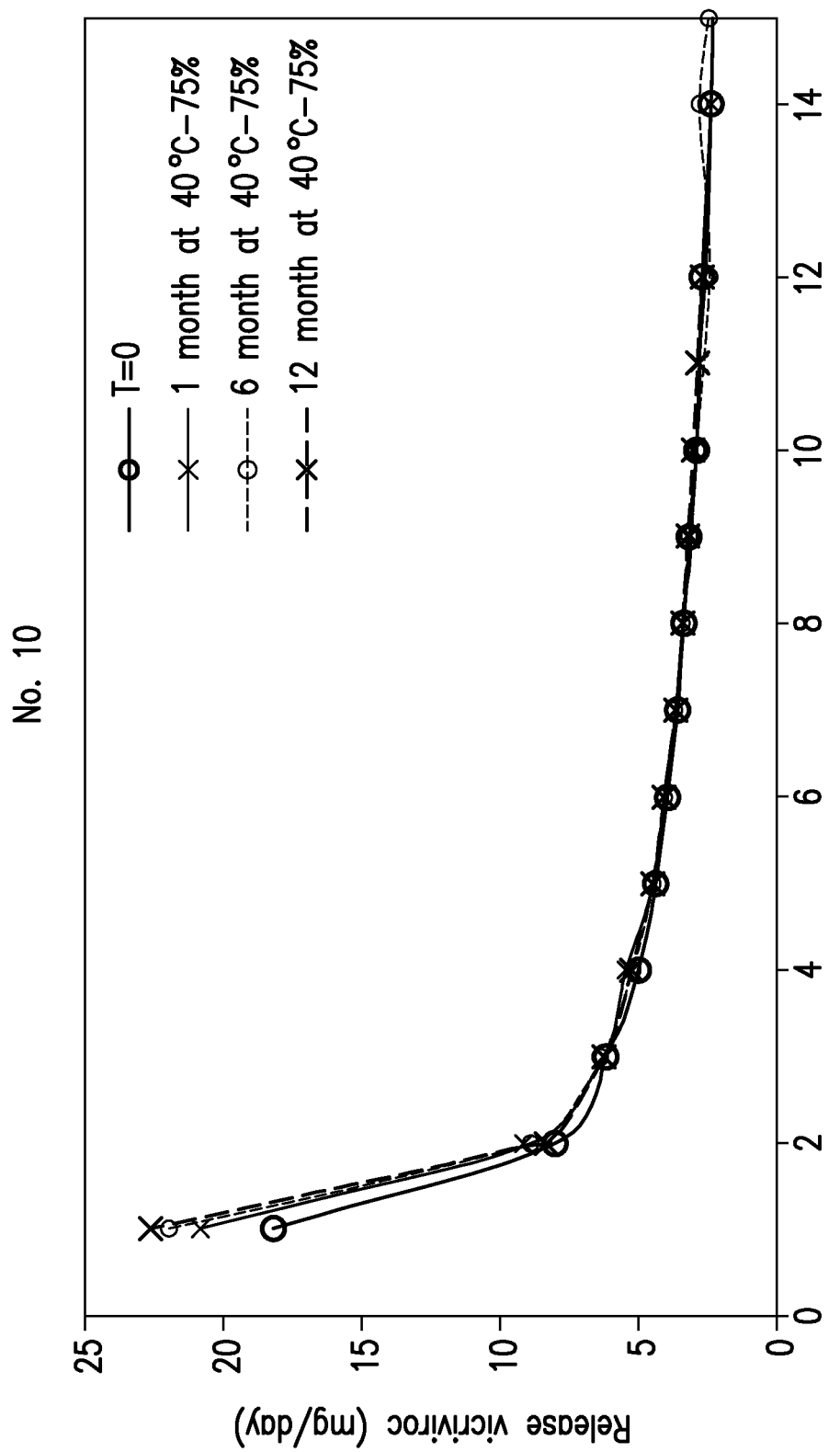
FIG. 17 shows the in vitro release of vicriviroc from vaginal ring drug delivery systems exemplified herein up to 12M storage at 40° C.
Figure 18:
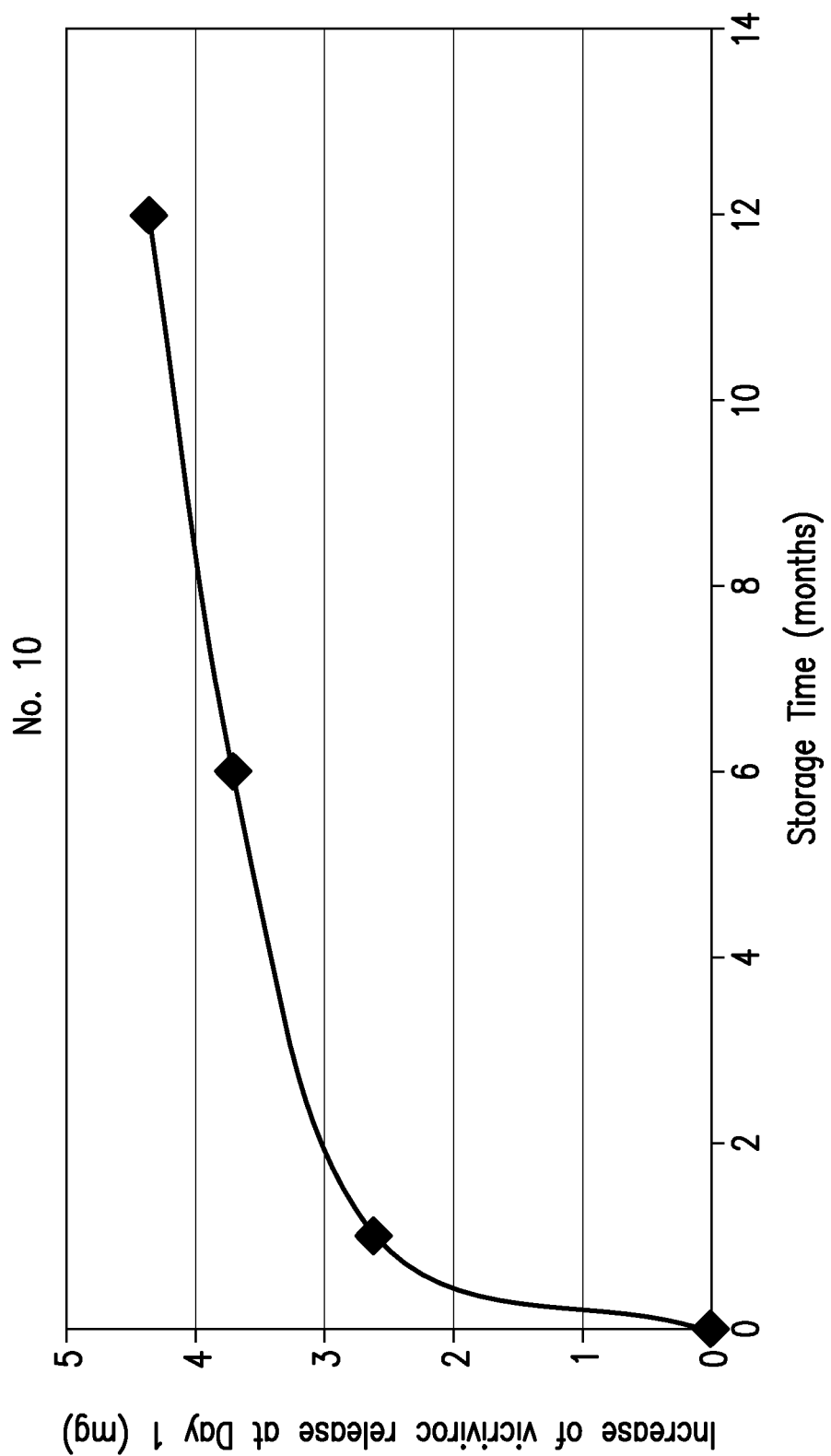
FIG. 18 shows the increase of vicriviroc on the day 1 release relative to t=0 from vaginal ring drug delivery systems exemplified herein.

FIGS. 15 and 16 show the in vitro release of vicriviroc of ring no. 4 and no. 8, respectively, up to 12 months storage at 30° C. For these rings, the in vitro release does not continuously increases due to the formation of deposits on the surface of the ring and can be considered physically stable. FIG. 17 shows the in vitro release of vicriviroc of ring no. 10 up to 12M storage at 40° C. and FIG. 18 shows the increase of the day 1 release of vicriviroc relative to t=0 of ring no. 10. The ring can be considered stable as the day release increase levels off during storage and the remainder of the profile is almost overlapping Example 8

Efficacy of Ring Segments

Vaginal rings with a core of EVA 28% and 10 wt % vicriviroc and a 50 μm skin with EVA 28 and 30 wt % MK-2048 were manufactured according to the process described in Example 1.

Ring segments were placed on an apical surface of ectocervical tissue with 100 μl of culture medium to allow for drug delivery. This was done on the day of culture set-up. Forty eight hours later, HIV-1 was added to the tissue apical surface. As controls, untreated explants (HIV-1 only) and explants treated with a single dose of vicriviroc (100 μM) and MK-2048 (100 μM or 10 μM) were included. API was added at the same time as HIV-1.

The ring segments containing vicriviroc, MK-2048 and vicriviroc/MK-2048 all prevented HIV-1 infection of the ectocervical tissue (8/8 explants remained IHC negative; Table 5). The control tissues which had no treatment and the tissue with the ring placebo segments all became infected.

TABLE 5

| Treatment | IHC (# neg/# total) | p24 % Inhibition |
|---|---|---|
| Placebo | 0/6 | 39% |
| Ring Segment with VCV | 8/8 | 74% |
| Ring Segment with MK-2048 | 8/8 | 72% |
| Ring Segment with VCV/MK-2048 | 8/8 | 69% |

IHC: immunohistochemistry, the IHC negative tissues/IHC total tissues tested.
% Inhibition: Percent inhibition. The data represent the reduction of cumulative p24 between the treated explant to the untreated control explants.

The invention claimed is:

1. A vaginal ring drug delivery system comprising (i) a core comprising a first ethylene-vinylacetate copolymer and vicriviroc, wherein the vicriviroc is dissolved in the first ethylene-vinylacetate copolymer, and (ii) a skin surrounding the core comprising a second ethylene-vinylacetate copolymer wherein the second ethylene-vinylacetate copolymer is the only polymer in the skin, and wherein the first ethylene-vinylacetate copolymer has a higher vinylacetate content than the second ethylene-vinylacetate copolymer, and (S)-2-(3-chloro-4-fluorobenzyl)-8-ethyl-10-hydroxy-N,6-dimethyl-1,9-dioxo-1,2,6,7,8,9-hexahydropyrazino [1',2':1,5]pyrrolo [2,3-d]pyridazine-4-carboxamide, wherein the (S)-2-(3-chloro-4-fluorobenzyl)-8-ethyl-10-hydroxy-N,6-dimethyl-1,9-dioxo-1,2,6,7,8,9-hexahydropyrazino [1',2':1,5]pyrrolo[2,3-d]pyridazine-4-carboxamide is loaded in the skin in solid form, such that a depletion layer is preformed, and upon release, the (S)-2-(3-chloro-4-fluorobenzyl)-8-ethyl-10-hydroxy-N,6-dimethyl-1,9-dioxo-1,2,6,7,8,9-hexahydropyrazino[1',2':1,5]pyrrolo [2,3-d]pyridazine-4-carboxamide loaded in the skin displays a near zero order release profile.

2. The drug delivery system of claim 1, wherein the first ethylene-vinylacetate copolymer has a vinylacetate content of 28% vinylacetate.

3. The drug delivery system of claim 1, wherein the second ethylene-vinylacetate copolymer has a vinylacetate content of 15% vinylacetate.

4. A vaginal ring drug delivery system comprising (i) a core comprising an ethylene-vinylacetate copolymer having a vinylacetate content of equal to or greater than 28% and vicriviroc, wherein the vicriviroc is in dissolved form, and (ii) a skin surrounding the core, wherein the skin comprises an ethylene-vinylacetate copolymer having a vinylacetate content of less than 28% wherein the ethylene-vinylacetate copolymer having a vinylacetate content of less than 28% is the only polymer in the skin, and (S)-2-(3-chloro-4-fluorobenzyl)-8-ethyl-10-hydroxy-N,6-dimethyl-1,9-dioxo-1,2,6,7,8,9-hexahydropyrazino[1',2':1,5]pyrrolo [2,3-d]pyridazine-4-carboxamide, wherein the (S)-2-(3-chloro-4-fluorobenzyl)-8-ethyl-10-hydroxy-N,6-dimethyl-1,9-dioxo-1,2,6,7,8,9-hexahydropyrazino[1',2':1,5]pyrrolo [2,3-d]pyridazine-4-carboxamide is loaded in the skin in solid form, such that a depletion layer is preformed, and upon release the (S)-2-(3-chloro-4-fluorobenzyl)-8-ethyl-10-hydroxy-N,6-dimethyl-1,9-dioxo-1,2,6,7,8,9-hexahydropyrazino[1',2':1,5]pyrrolo [2,3-d]pyridazine-4-carboxamide loaded in the skin displays a near zero order release profile.

5. The drug delivery system of claim 4, wherein the ethylene-vinylacetate copolymer in the core has a vinylacetate content between 28-33% vinylacetate.

6. The drug delivery system of claim 4, wherein the ethylene-vinylacetate copolymer in the core has a vinylacetate content of 28% vinylacetate.

7. The drug delivery system of claim 4, wherein the ethylene-vinylacetate copolymer in the skin has a vinylacetate content of 15% vinylacetate.

* * * * *